(12) United States Patent
King et al.

(10) Patent No.: US 12,324,661 B2
(45) Date of Patent: Jun. 10, 2025

(54) ADHERENCE-INDEPENDENT HOME HEALTH MONITOR SYSTEM

(71) Applicant: The Regents of the University of California, Oakland, CA (US)

(72) Inventors: Kevin King, San Diego, CA (US); Nicholas Harrington, San Diego, CA (US); Todd Coleman, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 490 days.

(21) Appl. No.: 17/419,662

(22) PCT Filed: Dec. 31, 2019

(86) PCT No.: PCT/US2019/069160
§ 371 (c)(1),
(2) Date: Jun. 29, 2021

(87) PCT Pub. No.: WO2020/142562
PCT Pub. Date: Jul. 9, 2020

(65) Prior Publication Data
US 2022/0071511 A1    Mar. 10, 2022

Related U.S. Application Data

(60) Provisional application No. 62/786,914, filed on Dec. 31, 2018.

(51) Int. Cl.
*A61B 5/11*    (2006.01)
*A61B 5/00*    (2006.01)
(Continued)

(52) U.S. Cl.
CPC .......... *A61B 5/1102* (2013.01); *A61B 5/0205* (2013.01); *A61B 5/0816* (2013.01);
(Continued)

(58) Field of Classification Search
None
See application file for complete search history.

(56) References Cited

U.S. PATENT DOCUMENTS 5,964,720 A * 10/1999 Pelz ..................... A61B 5/6887
600/595
8,731,646 B2 * 5/2014 Halperin ................. A61B 5/11
600/509

(Continued)

OTHER PUBLICATIONS

Inan et al., "Ballistocardiography and Seismocardiography: A Review of Recent Advances," Jul. 2015, IEEE Journal of Biomedical and Health Informatics, vol. 19, No. 4, pp. 1414-1427. (Year: 2015).*

(Continued)

*Primary Examiner* — Michael W Kahelin
*Assistant Examiner* — Luke M Stanley
(74) *Attorney, Agent, or Firm* — Mintz, Levin, Cohn, Ferris, Glovsky and Popeo, P.C.

(57) ABSTRACT

A health monitor system is provided. The health monitor system is a non-contact, adherence-independent home health monitoring system that longitudinally quantifies dynamic forces across diverse amplitudes and time scales to measure weight, respirations, and ballistocardiograms each night, as people sleep in the comfort of their home beds. Weights and respiratory signals are demixed even when users share the bed with a partner or pet. The incorporated technology is scalably manufacturable and thus inexpensive compared to implantable medical devices intended for the same purpose.

17 Claims, 24 Drawing Sheets

(51) Int. Cl.
  *A61B 5/0205* (2006.01)
  *A61B 5/08* (2006.01)
(52) U.S. Cl.
  CPC .......... *A61B 5/0826* (2013.01); *A61B 5/1115* (2013.01); *A61B 5/1116* (2013.01); *A61B 5/6891* (2013.01); *A61B 5/7207* (2013.01); *A61B 5/7253* (2013.01); *A61B 2505/07* (2013.01); *A61B 2560/0223* (2013.01)

(56) References Cited

U.S. PATENT DOCUMENTS

| | | | | |
|---|---|---|---|---|
| 8,905,928 | B2* | 12/2014 | Hayes | G16H 50/20 600/300 |
| 9,449,493 | B2 | 9/2016 | Shinar et al. | |
| 2005/0124864 | A1* | 6/2005 | Mack | A61B 5/6892 600/587 |
| 2014/0371635 | A1* | 12/2014 | Shinar | G08B 21/0211 600/595 |
| 2016/0174892 | A1 | 6/2016 | Benson et al. | |
| 2017/0067774 | A1 | 3/2017 | Gough et al. | |
| 2017/0188869 | A1* | 7/2017 | Kale | A61B 5/335 |
| 2019/0357854 | A1* | 11/2019 | Reich | G16H 50/50 |
| 2020/0110194 | A1* | 4/2020 | Young | A61B 5/1115 |
| 2020/0146910 | A1* | 5/2020 | Demirli | A61G 7/05753 |

OTHER PUBLICATIONS

Chaudhry, S.I. et al., "Patterns of weight change preceding hospitalization for heart failure." Circulation. 2007;116(14):1549-54.
Chaudhry, S.I. et al., "Telemonitoring in patients with heart failure." The New England Journal of Medicine. 2010;363(24):2301-9.
Jencks, S. F. et al., "Rehospitalizations among patients in the Medicare fee-for-service program." The New England journal of medicine. 2009;360(14):1418-28.
Miller, W. L. et al., "Understanding the heterogeneity in volume overload and fluid distribution in decompensated heart failure is key to optimal volume management: role for blood volume quantitation." J Am Coll Cardiol HF Jun. 2014;2(3):298-305.
Mozaffarian D, et al., "Heart disease and stroke statistics—2015 update: a report from the American Heart Association." on behalf of the American Heart Association Statistics Committee and Stroke Statistics Subcommittee. Circulation. Jan. 27, 2015;131(4):e29-322.
Pyenson, B. S. et al., "The high cost of heart failure for health systems: Opportunities for better management." Jul. 22, 2015. http://us.milliman.com/uploadedFiles/insight/2015/high-cost-heart-failure.pdf.
Yancy, C.W. et al., "2013 ACCF/AHA guideline for the management of heart failure: a report of the American College of Cardiology Foundation/American Heart Association Task Force on Practice Guidelines." Journal of the American College of Cardiology. 2013;62(16):e147-239.
International Search Report and Written Opinion issued in International Application No. PCT/US2019/069160, mailed Mar. 18, 2020 (Mar. 18, 2020). 12 pages.

\* cited by examiner

300    Calibration by moving
       a constant weight

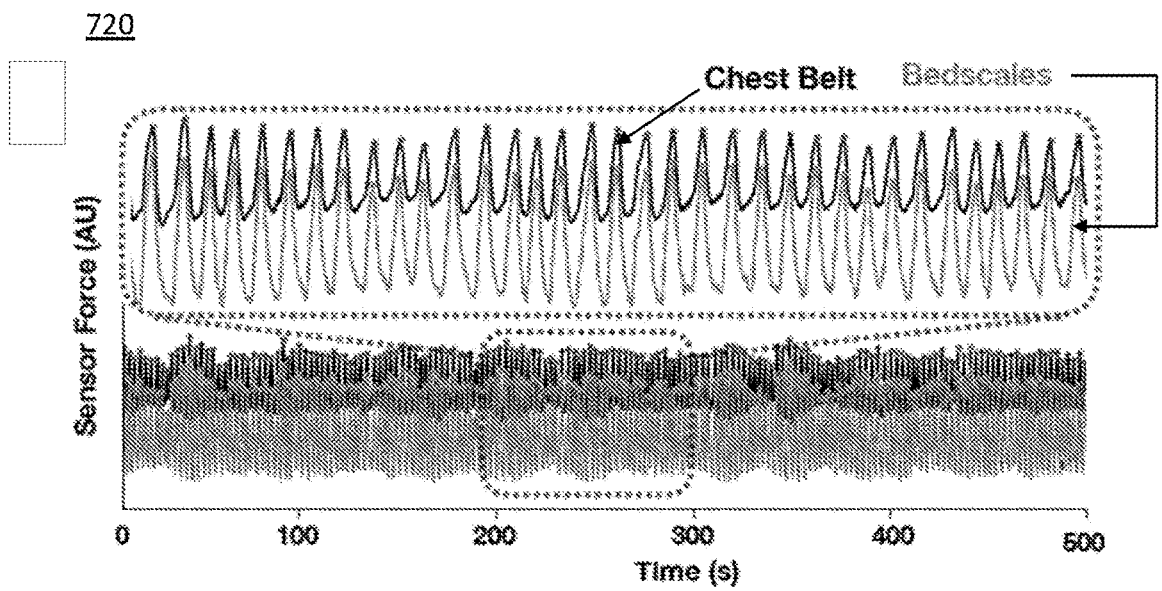
FIG. 7C
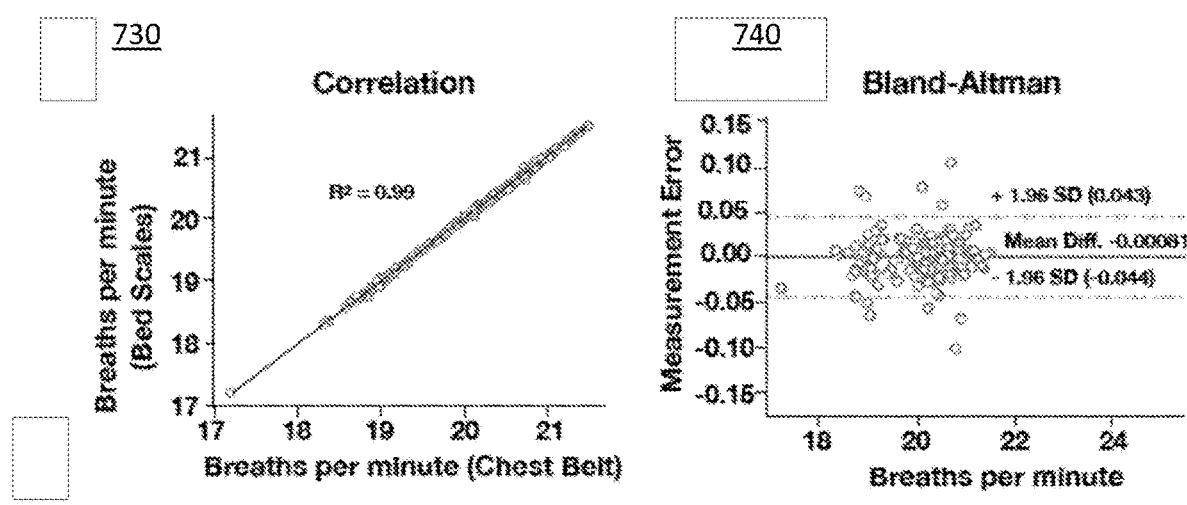
FIG. 7D
FIG. 7E

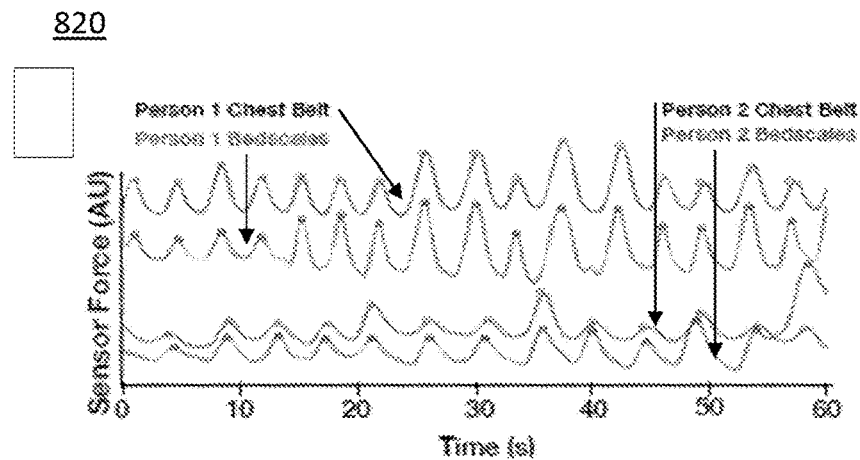
FIG. 8C
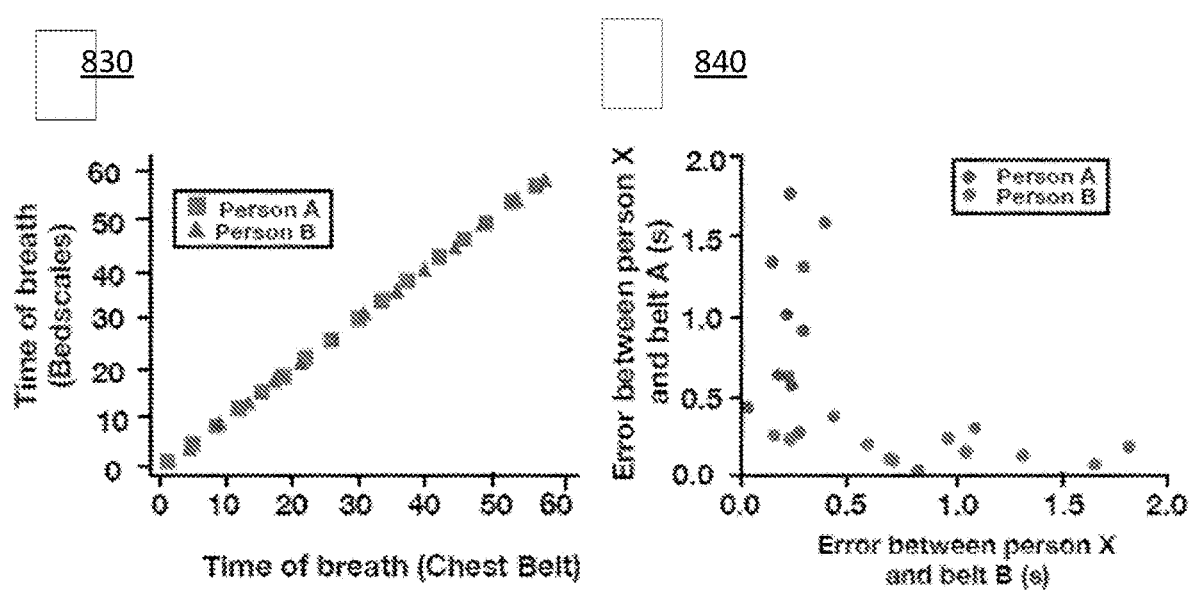
FIG. 8D
FIG. 8E

ADHERENCE-INDEPENDENT HOME HEALTH MONITOR SYSTEM

CROSS-REFERENCE TO RELATED APPLICATION

This application is a national phase entry of Patent Cooperation Treaty Application No. PCT/US2019/069160 filed Dec. 31, 2019, entitled "ADHERENCE-INDEPENDENT HOME HEALTH MONITOR SYSTEM," which claims priority to U.S. Provisional Patent Application No. 62/786,914 filed Dec. 31, 2018 and entitled "ADHERENCE-INDEPENDENT HOME HEALTH MONITOR," the disclosures of both of which are incorporated herein by reference in their entirety.

FIELD

The present disclosure relates to a health monitor system.

BACKGROUND

A monitoring system that may be easily installed and that provides for non-invasive measuring of health data related to a patient is desired to address deficiencies in current systems. In particular, a monitoring system that utilizes force measurements of a patient while the patient is sleeping or resting, without requiring patient intervention or action, leading to increased adherence, is desired. Moreover, a monitoring system that provides for separation of health data from multiple users, including pets, and that is compatible with a diverse environment is desired.

SUMMARY

Methods, systems, and articles of manufacture, including computer program products, are provided for a health monitor system that monitors and learns signature of early exacerbations and impending hospitalizations by passively collecting data without the requirement for daily patient engagement with technology in the home.

According to an aspect, a system includes a plurality of sensors, each of the plurality of sensors configured to engage with an article on which a first user is positioned, and each of the plurality of sensors configured to measure force. The system further includes a communication module in communication with each of the plurality of sensors, where the communication module receives force data transmitted from each of the plurality of sensors. The system further includes an apparatus including at least one data processor, and at least one memory storing instructions which, when executed by the at least one data processor, cause the apparatus to at least: receive, from the communication module, the force data; transform, in response to a change in the force data indicative of a change in a load on the article and based on a determination of a plurality of physiological sources on the article, the force data from each of the plurality of sensors into a corresponding plurality of physiological signals; and determine, based on the plurality of physiological signals, a source physiological signal for each of the plurality of physiological sources. The determination of the source physiological signal for each of the plurality of physiological sources includes separating into components each of the plurality of physiological signals, where the components correspond to each of the plurality of physiological sources at each of the plurality of sensors, and compositing the separated components for each of the plurality of physiological sources, where the compositing forms the source physiological signal for each of the plurality of physiological sources.

According to an aspect, a method includes receiving, by a remote processing device and from a communication module in communication with a plurality of sensors, force data. Each of the plurality of sensors is configured to engage with a member of an article on which a first user is positioned, and each of the plurality of sensors is configured to measure force. The method further includes transforming, by the remote processing device and in response to a change in the force data indicative of a change in a load on the article and based on a determination of a plurality of physiological sources on the article, the force data from each of the plurality of sensors into a corresponding plurality of physiological signals. The method further includes determining, by the remote processing device and based on the plurality of physiological signals, a source physiological signal for each of the plurality of physiological sources. The determination of the source physiological signal for each of the plurality of physiological sources includes separating into components each of the plurality of physiological signals, where the components correspond to each of the plurality of physiological sources at each of the plurality of sensors, and compositing the separated components for each of the plurality of physiological sources, where the compositing forms the source physiological signal for each of the plurality of physiological sources.

According to an aspect, an apparatus includes at least one data processor, and at least one memory storing instructions which, when executed by the at least one data processor, cause the apparatus to at least receive, from a communication module in communication with a plurality of sensors, force data. Each of the plurality of sensors is configured to engage with a member of an article on which a first user is positioned, and each of the plurality of sensors is configured to measure force. Execution of the instructions further causes the apparatus to transform, in response to a change in the force data indicative of a change in a load on the article and based on a determination of a plurality of physiological sources on the article, the force data from each of the plurality of sensors into a corresponding plurality of physiological signals; and determine, based on the plurality of physiological signals, a source physiological signal for each of the plurality of physiological sources. The determination of the source physiological signal for each of the plurality of physiological sources includes separating into components each of the plurality of physiological signals, where the components correspond to each of the plurality of physiological sources at each of the plurality of sensors, and compositing the separated components for each of the plurality of physiological sources, where the compositing forms the source physiological signal for each of the plurality of physiological sources.

According to an aspect, a non-transitory computer-readable storage medium includes program code, which when executed by at least one data processor, causes operations including: receiving, by a remote processing device and from a communication module in communication with a plurality of sensors, force data, where each of the plurality of sensors is configured to engage with a member of an article on which a first user is positioned, and further where each of the plurality of sensors is configured to measure force; transforming, by the remote processing device and in response to a change in the force data indicative of a change in a load on the article and based on a determination of a plurality of physiological sources on the article, the force data from each of the plurality of sensors into a corresponding plurality of physiological signals; and determining, by the remote processing device and based on the plurality of physiological signals, a source physiological signal for each of the plurality of physiological sources. The determination of the source physiological signal for each of the plurality of physiological sources includes separating into components each of the plurality of physiological signals, where the components correspond to each of the plurality of physiological sources at each of the plurality of sensors, and compositing the separated components for each of the plurality of physiological sources, where the compositing forms the source physiological signal for each of the plurality of physiological sources.

According to an aspect, an apparatus includes means for receiving, from a communication module in communication with a plurality of sensors, force data, where each of the plurality of sensors is configured to engage with a member of an article on which a first user is positioned, and further where each of the plurality of sensors is configured to measure force; means for transforming, in response to a change in the force data indicative of a change in a load on the article and based on a determination of a plurality of physiological sources on the article, the force data from each of the plurality of sensors into a corresponding plurality of physiological signals; and means for determining, based on the plurality of physiological signals, a source physiological signal for each of the plurality of physiological sources. The means for determining the source physiological signal for each of the plurality of physiological sources includes means for separating into components each of the plurality of physiological signals, where the components correspond to each of the plurality of physiological sources at each of the plurality of sensors, and means for compositing the separated components for each of the plurality of physiological sources, where the compositing forms the source physiological signal for each of the plurality of physiological sources.

In some variations, one or more of the features disclosed herein including the following features can optionally be included in any feasible combination. The determination of the source physiological signal for each of the plurality of physiological sources may be based on a model for each of the plurality of physiological sources, where each model includes the components, the components defining a contribution of a respective physiological source to each of the plurality of physiological sources. Based on the determination of the plurality of physiological sources on the article, the physiological signals may be based on the force data from at least two of the plurality of sensors. The force data may be continuously transmitted from the communication module to the apparatus, and changes to the force data may be continuously monitored. Transforming the force data may include time-domain and/or frequency-domain filtering the force data to obtain a plurality of respiratory signals corresponding to each of the plurality of sensors. A source respiratory signal may be determined, based on the plurality of respiratory signals, for each of the plurality of physiological sources, and one or more respiratory parameters may be identified from the source respiratory signal for each of the plurality of physiological sources. Transforming the force data may include time-domain and/or frequency-domain filtering the force data to obtain a plurality of ballistocardiogram signals corresponding to each of the plurality of sensors. A source ballistocardiogram signal may be determined, based on the plurality of ballistocardiogram signals, for each of the plurality of physiological sources, and one or more ballistocardiogram parameters may be identified from the source ballistocardiogram signal for each of the plurality of physiological sources. The change in the force data indicative of the change in the load on the article may be determined based on identifying the change in the force data greater than a predefined threshold of force for a predefined duration threshold. The determination of the plurality of physiological sources on the article may be based on identification of alterations in the physiological signals transformed from the force data. An amount of time on the article for one or more of the plurality of physiological sources may be determined, where the amount of time is determined based on transitions on and off the article, where the transitions are tracked by monitoring alterations in the force data. Movements made by one or more of the plurality of physiological sources may be determined, where the movements are tracked by monitoring signal variance and/or amplitude of the force data. The apparatus may include a remote cloud-based server. The plurality of sensors and the communication module may include a wired connection. Each of the plurality of sensors may include force-sensing strain gauge transducers configured in a strain gauge sensing circuit configuration. Each of the plurality of sensors may include a rigid top plate configured to engage with the article; foot and flexure spring elements configured to engage with the force-sensing strain gauge transducers; and a rigid bottom plate configured to engage with a floor. The foot and flexure spring elements and the force-sensing strain gauge transducers may be at least partially contained in a volume defined by the rigid top plate at an upper end and the rigid bottom plate at a lower end.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 7A-FIG. 7E illustrate aspects related to respiratory monitoring consistent with implementations of the current subject matter;

FIG. 8A-FIG. 8E illustrate aspects of demixing respiratory signals consistent with implementations of the current subject matter;

Figure 1A:
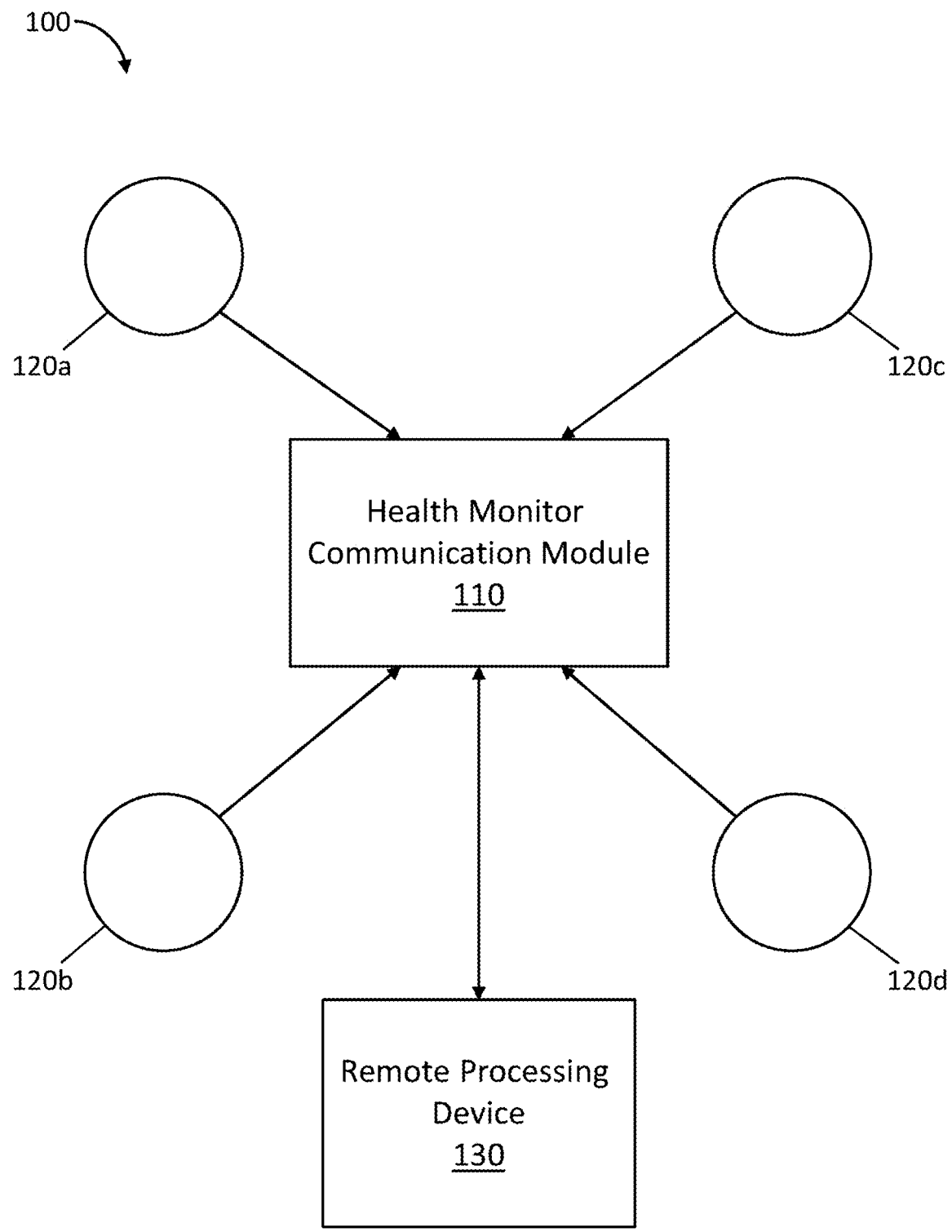
FIG. 1A is a block diagram representation of a health monitor system consistent with implementations of the current subject matter.

Like labels are used to refer to same or similar items in the drawings.

DETAILED DESCRIPTION

Aspects of the current subject matter relate to a health monitor system, and more particularly to a home health monitor system that is non-invasive and adherence-independent from the perspective of a user (also referred to herein as a patient). For example, the home health monitor system (also referred to herein as the heath monitor system) consistent with implementations of the current subject matter may not require the patient to perform or otherwise be involved in actions with respect to regular use of the health monitor system. The health monitor system consistent with implementations of the current subject matter includes one or more sensors that monitor the patient while the patient is situated or otherwise positioned on a surface, such as a bed, couch, chair, or the like. More particularly, one or more sensors longitudinally measure cardiopulmonary biomarkers of daily weight, as well as dynamic physiologic signals of respiratory and ballistocardiographic origin without requiring any active patient participation.

Moreover, aspects of the current subject matter include algorithms that enable automated in situ calibration and automated continuous decoupling of weight, respirations cardiac signals, and movements from two persons sharing a bed. By overcoming home monitoring adherence barriers, aspects of the current subject matter disclosed herein may identify signatures of exacerbation and impending hospitalization, and thus facilitate optimization of outpatient chronic disease management.

The human body is in continuous motion. From early in development until the last day of life, our bodies exert a wide range of static and dynamic mechanical forces on the environment. Under most conditions, large musculoskeletal forces obscure lower amplitude physiologic forces resulting from respirations or the ballistic motion of the beating heart. However, when a person is asleep, musculoskeletal motion quiets for extended periods of time, allowing longitudinal monitoring of dynamic physiology for many hours every day within the comfort of, for example, a person's home bed. Thus, aspects of the current subject matter utilize a setting in which a patient is asleep and in which longitudinal monitoring of dynamic physiology may be achieved for chronic disease monitoring and management tools.

Cardiopulmonary diseases are among the most challenging chronic conditions to manage. Heart failure, for example, affects 6 million patients in the United States and costs more than $30B per year largely due to the high burden of inpatient care required for management of recurrent exacerbations. Most hospitalizations for heart failure are related to worsening congestion that drives symptoms of dyspnea, fatigue, and edema that progressively limit physical activity. It is believed that many of these hospitalizations could be prevented with better strategies for early identification of worsening fluid retention to direct early intervention with pharmacological therapy.

Traditional home health monitoring technologies promise to improve care and reduce costs, yet they are limited by the need for adherence to self-monitoring, usage of an application, and/or application of a wearable device or component. While implantable sensors may overcome the adherence barrier, they are expensive and require invasive procedures.

More specifically, current strategies for remote heart failure management focus on telemonitoring strategies that emphasize regular surveillance of daily weights and changes in vital signs and respiratory symptoms. These strategies frequently rely on a high degree of patient engagement and self-monitoring, and most studies have accordingly shown little incremental impact on rates of hospitalization and death in heart failure patients when compared with usual clinic-based care. The need for adherence to self-application of wearables and patient-initiated utilization of applications ("apps") also limits their generalized utility as home health monitors. Implantable hemodynamic monitors, such as the CardioMEMS™ pulmonary artery pressure sensor, have been developed to overcome adherence barriers and provide access to more detailed physiologic data to guide heart failure management. This approach, however, is challenging to scale for population health management given the need for an invasive procedure to implant the sensor and high associated costs, and still requires adherence to a daily schedule of data transmission by the patient. Newer remote monitoring approaches overcome adherence barriers by leveraging software modifications to existing cardiac rhythm management devices to provide multi-parameter monitoring of physiologic signals including heart rate, heart sounds, respiration, physical activity, and intrathoracic impedance that can be integrated to anticipate worsening heart failure events. While this approach is being tested in clinical trials as a strategy for routine heart failure management, it is not likely to be helpful for the large proportion of health failure patients (particularly those with preserved ejection fraction) who do not require implantable pacemakers and defibrillators.

Non-contact sensors have been developed using under-the-mattress piezoelectric-based, strain gauge-based, or radio frequency-based sensing. However, such non-contact sensors are sensitive to subject-sensor proximity and orientation and are unable to reliably differentiate signals from individuals who share a bed with a partner or pet. Moreover, because these sensors do not span the entire bed, they are also unable to measure total body weight. Sensors beneath the bed legs have not been compatible with uneven or deformable surfaces, such as carpeted floors. Furthermore, generalizable methods have not been developed to robustly separate weights and dynamic physiological signals from multiple persons based on data from bed leg-based sensors.

Aspects of the current subject matter may overcome these and other deficiencies. In particular, aspects of the current subject matter provide for monitoring and learning signatures of early exacerbations and of impending hospitalizations, thereby preventing or reducing hospitalization. The health monitor system of the current subject matter employs a non-invasive, multi-parameter measurement technology that passively collects data without the requirement for daily patient engagement with technology in the home, thereby improving limitations of existing remote monitoring technologies for heart failure. Additionally, the health monitor system of the current subject matter takes into account total body weight, which is a pervasively-used objective biomarker of worsening congestion that can be quantified in the home.

Consistent with implementations of the current subject matter, features of the health monitor system provide for an under-the-bed (or other article on which a patient may be positioned, such as a couch, chair, or the like) mechanical sensing platform that achieves non-invasive, adherence-independent, non-contact longitudinal physiological monitoring of total body weight, respirations, and ballistocardiograms (BCG). Signals are passively acquired during sleep, without the need for patient participation, even if the bed is shared by a partner or pet. Algorithms consistent with implementations of the current subject matter demix weight and physiological signals when the bed is shared by a partner or a pet. The health monitor system quantitatively characterizes central and obstructive sleep apneas, and discriminates atrial fibrillation from normal sinus rhythm. By eliminating the need for patient participation, the health monitor system with non-contact health sensors improves care of patients with difficult-to-manage chronic cardiopulmonary diseases, such as heart failure.

While various implementations consistent with the current subject matter may be described with reference to a bed, the implementations are not so limited to such a configuration. In particular, aspects of the current subject matter may be implemented with other articles on which one or more patients may be positioned or otherwise situated. For example, in addition to a bed, aspects of the current subject matter may be implemented with a couch, chair (e.g., an upright chair or a reclining chair), chaise, or the like. Moreover, while various implementations of the current subject matter may be described with reference to one or more bed legs, the implementations are not limited to bed legs. In particular, aspects of the current subject matter may be implemented with any downward extending member from the article on which the patient is positioned, or with a platform-type article that allows for balancing or positioning the platform-type article on one or more sensors at one or more points of contact. Consistent with implementations of the current subject matter, the downward extending member or the platform-type article helps support and distribute the weight of the patient.

Consistent with implementations of the current subject matter, sensors are positioned beneath legs of, for example, a conventional home bed, recliner, couch, or the like to perform longitudinal monitoring of total body weight, respirations, and ballistocardiograms. As typical patients may spend up to or more than 90% of their lives at home and up to or more than one third of their lives in bed, the arrangement of the sensors beneath the legs of the bed leverages the optimal diagnostic setting by facilitating monitoring when the patient is in bed (or situated on another like article). Thus, according to implementations of the current subject matter, the sensors of the health monitor system perform the monitoring operations without requiring patient participation for self-sensing, data-transmission, or application of a wearable device.

Figure 1B:
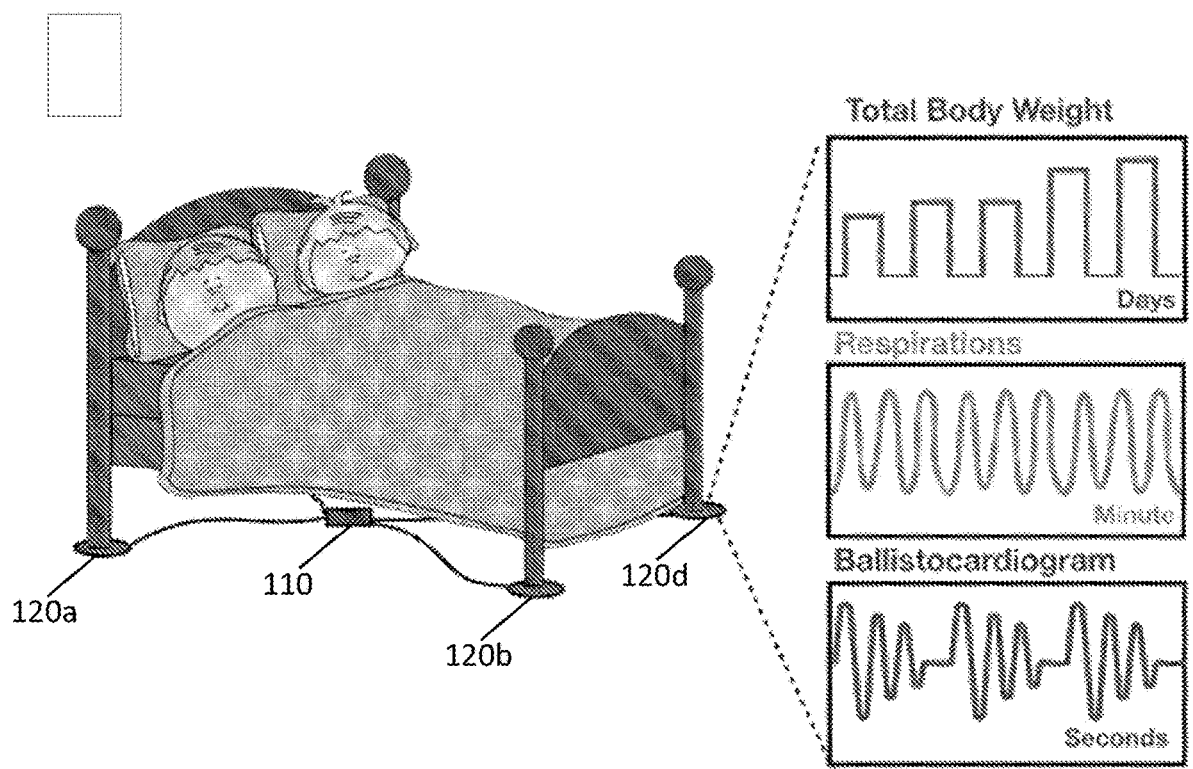
FIG. 1B is a representation of a health monitor system consistent with implementations of the current subject matter.

FIG. 1A is a block diagram representation of a health monitor system 100 consistent with implementations of the current subject matter. One or more sensors 120 are provided for positioning at one or more points of balance or contact of an article (e.g., beneath the legs of a bed, beneath an extending support member of a bed or other article, at one or more points of contact of a platform-type article). The sensors 120 are coupled to and in communication with a health monitor communication module 110, which is coupled to and in communication with a remote processing device 130. Although four sensors 120a, 120b, 120c, and 120d are shown, fewer or additional sensors 120 may be incorporated. For example, the number of sensors 120 may be dependent on the one or more points of balance or contact of the article (e.g., the number of legs or extending support members, or the number of points of contact of a platform-type article) of the surface on which the patient sleeps. In some implementations, the number of sensors 120 may be less than the number of legs or extending support members. FIG. 1B is an example representation of the health monitor system 100 utilized with a bed. Example weight, respirations, and ballistocardiogram measurements are also illustrated.

Figure 2A:
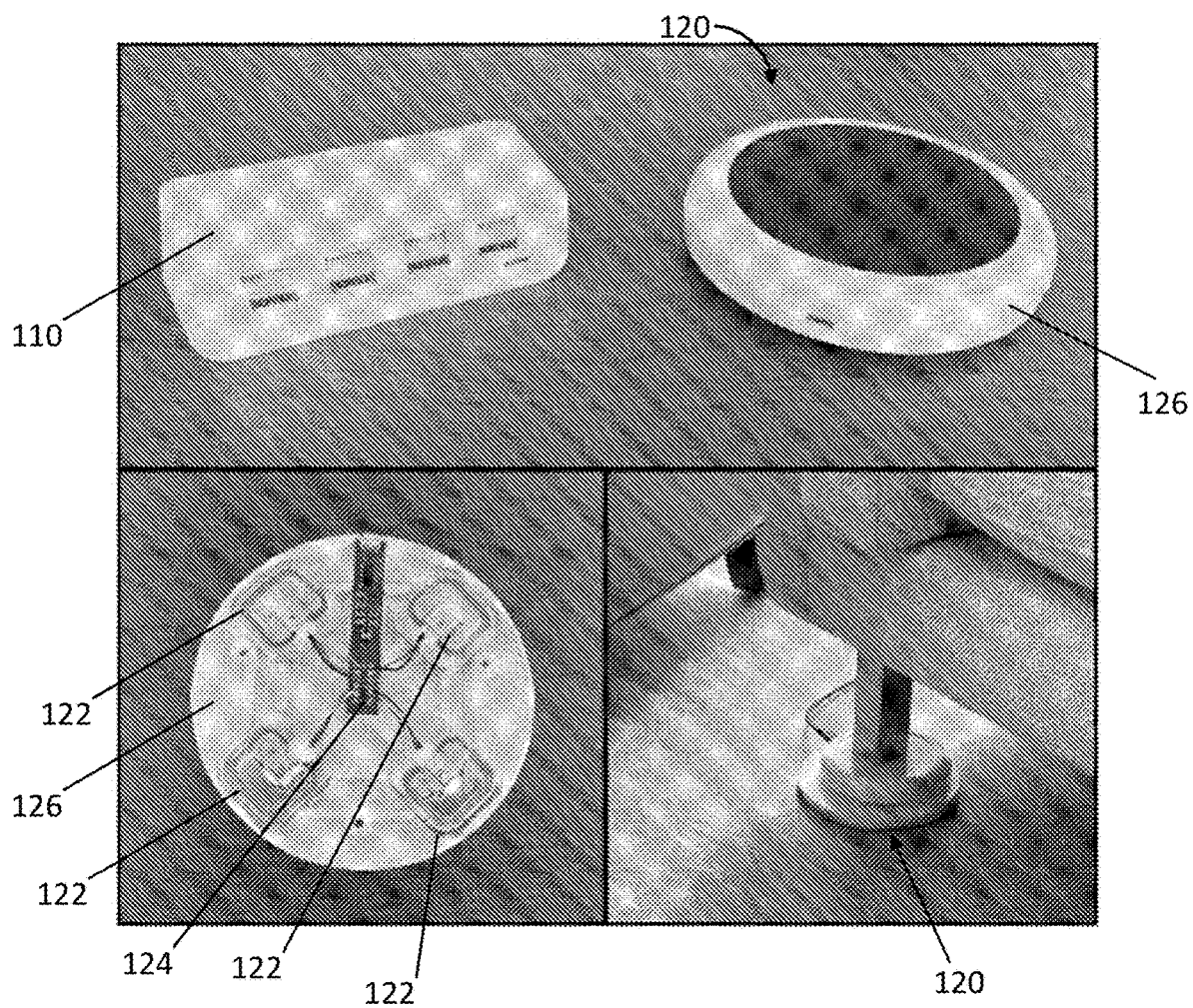
FIG. 2A-FIG. 2E are representations of various aspects of a health monitor system consistent with implementations of the current subject matter.
Figure 2B:
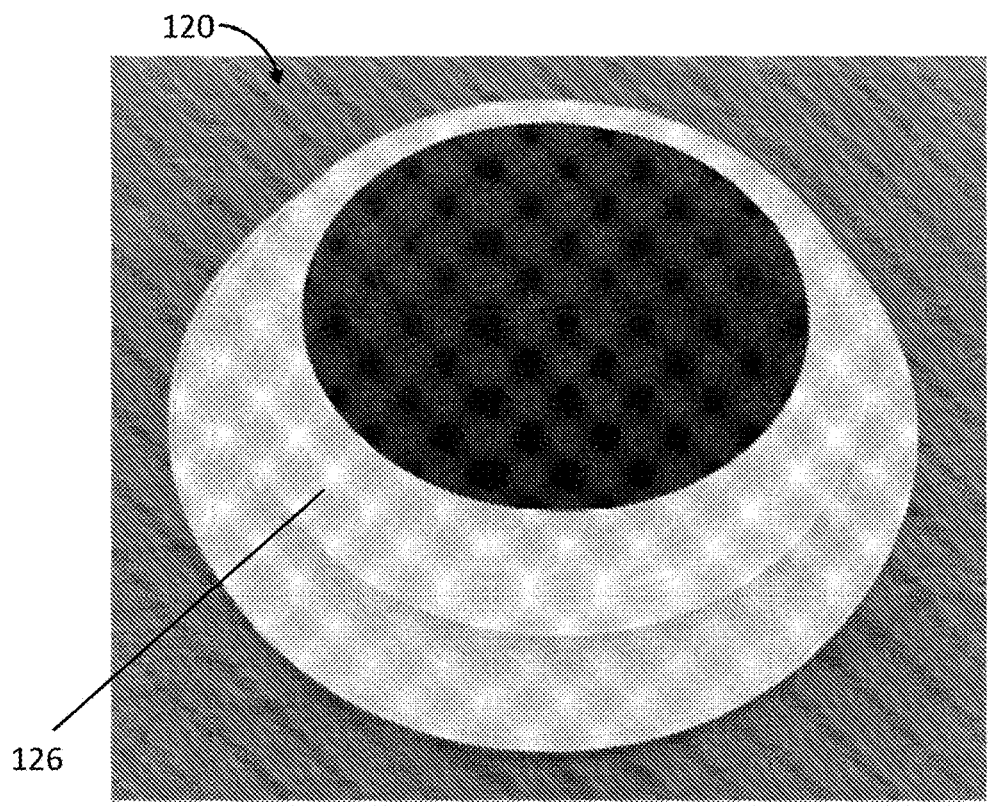
Figure 2C:
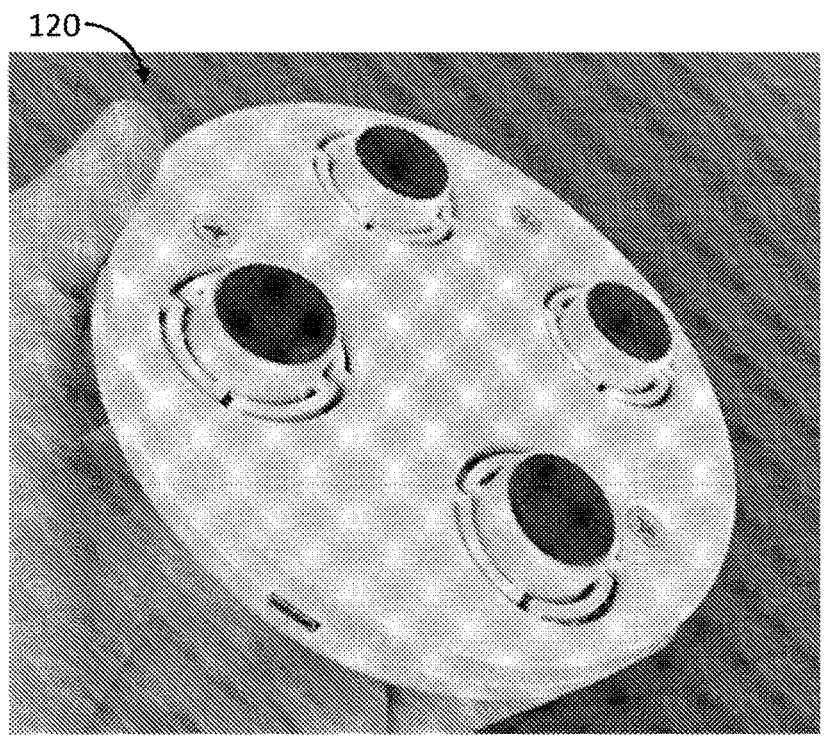
Figure 2D:
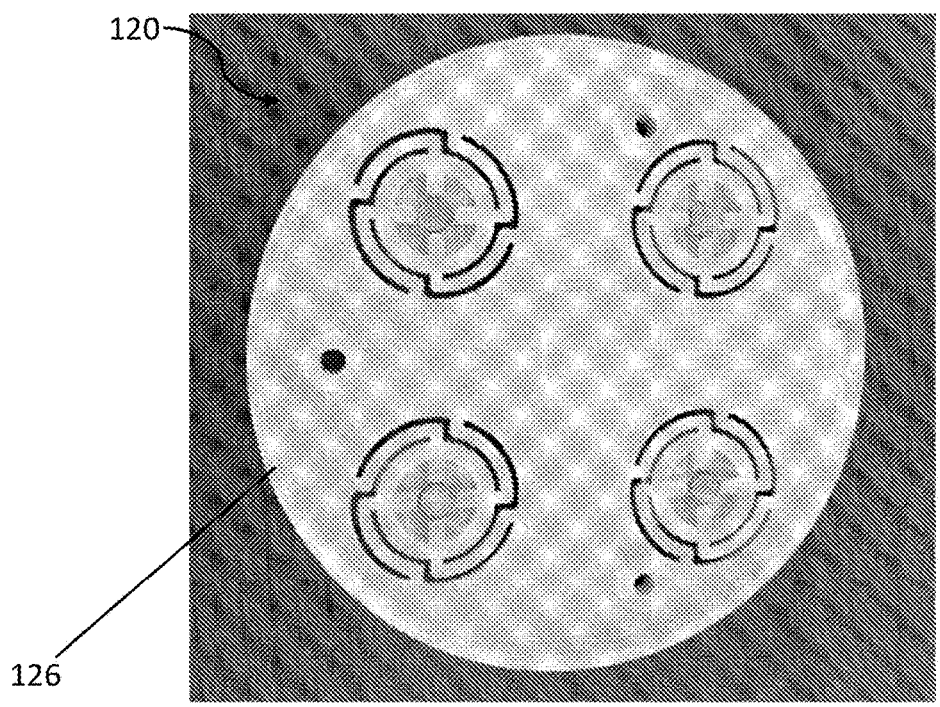

Each of the sensors 120 is, consistent with implementations of the current subject matter, a non-contact, low-profile sensor including force-sensing strain gauge transducers. The force-sensing strain gauge transducers may be configured in a strain gauge sensing circuit configuration, such as a Wheatstone bridge circuit or the like. The force-sensing strain gauge transducers measure a force being applied to the respective sensor 120. A signal corresponding to the measured force may be amplified and digitized by an analog-to-digital integrated circuit (e.g., a 24-bit analog-to-digital integrated circuit). With reference to FIG. 2A, a representation of one of the sensors 120 is provided. The force-sensing strain gauge transducers 122 are coupled to a circuit board 124 with the analog-to-digital integrated circuit and accompanying discrete circuit elements. The force-sensing strain gauge transducers 122 and the circuit board 124 fit (e.g., by a snap fit) into a housing 126, such as an injection-molded housing. The housing 126 may include a planar plastic flexure spring mechanism, which registers the sensor 120 with the housing 126 and focuses the entire load on the sensor 120 through the sensing elements (e.g., the force-sensing strain gauges 122) and minimizes shunting of force via the surrounding housing 126. As shown in FIG. 2B and FIG. 2C, each of the sensors 120 may include a rubber top and feet, or the like, to prevent lateral sliding. Consistent with some implementations of the current subject matter, a bottom plate (e.g., a rigid bottom plate of a circular, square, rectangular, or other polygonal shape) is added to provide a reliable surface for the sensor feet to contact (see FIG. 2A). The bottom plate allows the sensors 120 to be used in carpeted areas and, for example, to be outfitted with furniture pads or the like for use on uncarpeted floors. FIG. 2D provides a representation of the sensor 120 without the bottom plate. As shown, inserts or feet are provided as points of contact or engagement with the force-sensing strain gauge transducers.

Figure 2E:
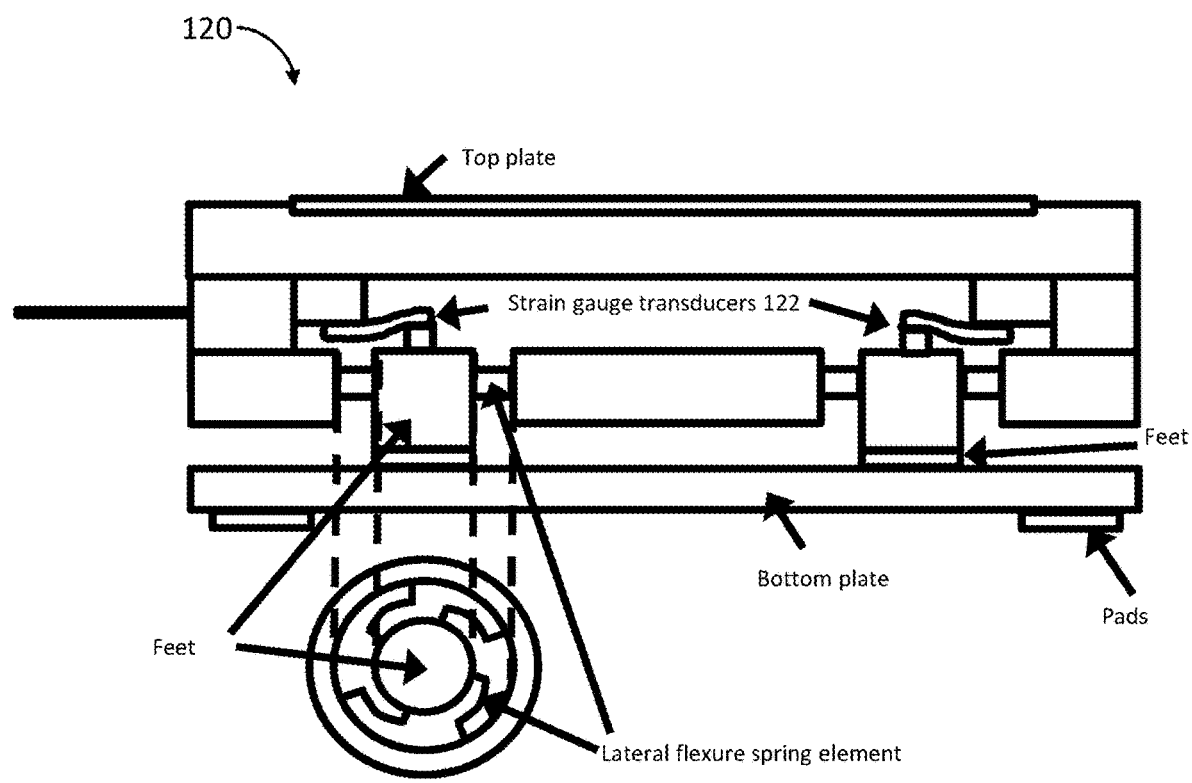

FIG. 2E illustrates additional aspects of the sensors 120 consistent with implementations of the current subject matter. A rigid top plate, configured to engage with the article, is provided as, for example, part of the housing 126. The rigid top plate may have a friction-inducing or adhesive surface to prevent lateral movement of the article. Foot and flexure spring elements are configured to engage with the force-sensing strain gauge transducers 122. A cross-sectional view is shown in FIG. 2E. The lateral flexure spring element serves to register the feet with respect to the housing 126 and the strain gauge transducers 122 via lateral forces without bearing vertical force, which is quantified by the strain gauge transducers 122. A bottom plate (e.g., a rigid bottom plate) is provided and is configured to engage with the floor to make it compatible with uneven or deformable surfaces and prevent interference with fibers from carpeting or the like. Feet (e.g., rubber feet) may be included to prevent sliding on the bottom plate. Alternatively, the feet may be fixed to a bottom surface of the bottom plate. As shown in FIG. 2E, the foot and flexure spring elements and the force-sensing strain gauge transducers 122 are contained in a volume defined by the top plate at an upper end and the bottom plate at a lower end. Consistent with implementations of the current subject matter, the foot and flexure spring elements and the force-sensing strain gauge transducers 122 may be partially contained in the volume defined by the top pate and the bottom plate. For example, the top plate and/or the bottom plate need not cover or contain the components in their entirety.

With further reference to FIG. 1A and FIG. 2A, digitized and amplified data from the individual sensors 120 is transmitted to the health monitor communication module 110 (also referred to herein as the communication module 110). The transfer of data may be via, for example, micro universal serial bus (USB) (see the communication module 110 in FIG. 2A) using, for example, a Raspberry Pi. Other architectures may be utilized for the data transfer between the sensors 120 and the communication module 110. Aspects of the current subject matter may incorporate a hardwired solution (e.g., the micro USB connection) over wireless or Bluetooth so that patients are not required to re-establish communication if, for example, Bluetooth pairing is lost. The communication module 110 may require the use of wall power, thereby eliminating constraints on the duration of data collection and avoiding the need for battery changes. The wall power connection of the communication module 110 as well as the hardwired connection between the sensors 120 and the communication module 110 provides for the health monitor system 100 assuming nothing about a patient's technical literacy or "connectedness" and only requires that a patient have electricity in the home, making it suitable to address management challenges in patients who are socioeconomically disadvantaged, geographically separated from providers, and/or cognitively impaired.

The communication module 110 includes memory and a processor to store and process the data from the sensors 120. After local signal conditioning or processing (e.g., to detrend, de-spike, de-noise, or the like the data) at the communication module 110, the data may be communicated to the remote processing device 130. For example, consistent with implementations of the current subject matter, the communication module 110 may also include wireless communication circuitry to transfer the data to the remote processing device 130. The remote processing device 130 may be, for example, a cloud-based server such as HIPAA-affiliate Amazon Web Services. Other cloud-based servers may be utilized with aspects of the current subject matter. The communication between the communication module 110 and the remote processing device 130 may be via, for example, WiFi. If a local internet connection is unavailable, the communication between the communication module 110 and the remote processing device 130 may be via a HIPAA-affiliate 3G cellular data transmission device or the like. The sensor measurement and the transfer of data by the health monitor system 100 is self-sufficient and does not require an accompanying user device, such as a mobile device or laptop computer, and user actions. Once the data is stored at the remote processing device 130 (e.g., in the cloud), the data can be synchronously or asynchronously processed to create custom analytics, visualizations, and dashboards for permission-dependent sharing with patients, healthcare providers, or family and friends.

Consistent with implementations of the current subject matter, the remote processing device 130 may be remote in that it is separate from the communication module 110. For example, the remote processing device 130 may be a computing device located in the same room or building as the communication module 110. According to aspects of the current subject matter, the communication module 110 may include the remote processing device 130. According to aspects of the current subject matter, a portion of the processing described herein with respect to force data may be done by the communication module 110, while another portion of the processing may be implemented by the remote processing device 130.

Consistent with implementations of the current subject matter, the health monitor system 100 measures the distributed weight of the load (e.g., the bed and its contents) such that the total load is proportional to the sum of the individual bed leg measurements. The health monitor system 100 may perform continuous monitoring, which allows each load to be separately weighed at the time it is added. When an object of constant weight is moved to different locations on the bed, its load redistribution changes but the total remains constant.

Figure 3A:
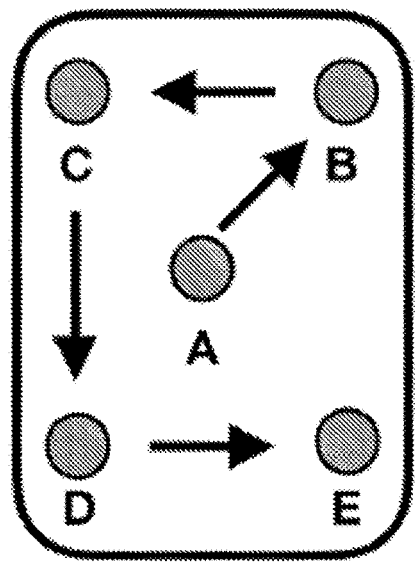
FIG. 3A-FIG. 3B illustrate a load calibration mechanism consistent with implementations of the current subject matter.
Figure 3B:
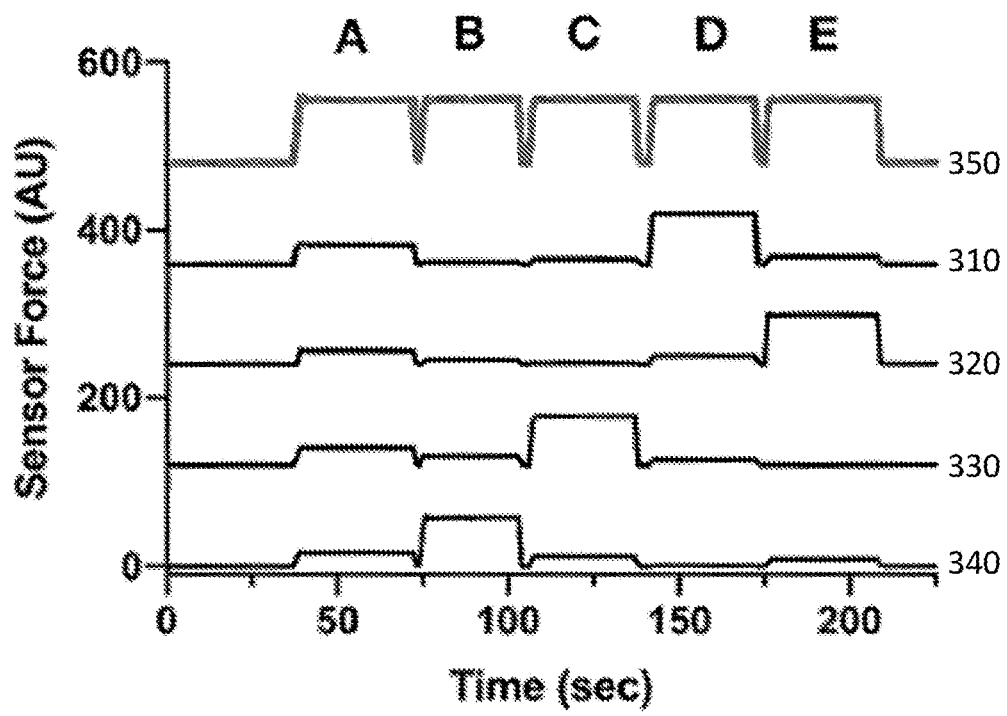

The health monitor system 100 may be calibrated at the time of installation. For example and with reference to diagram 300 of FIG. 3A and curves 310, 320, 330, 340, and 350 of FIG. 3B, an object of known weight (e.g., 25 pounds) may be moved to N+1 locations (where N is the number of bed legs) while making continuous measurements. FIG. 3A illustrates redistribution of a constant load on a bed (e.g., movement of a load from positon A to position B, to position C, to position D, and to position E). FIG. 3B represents load measured by each of the four sensors 120 positioned beneath four bed legs (the four bottom curves in FIG. 3B (310, 320, 330, 340)), and the sum of the loads measured by the four sensors 120 (the top curve in FIG. 3B (350)). The calibration may assume a linear model to solve for the calibration factors, as shown in FIG. 3A and FIG. 3B.

As an alternative calibration process, calibration may be performed using a person's known weight at one time point combined with redistributions of weight during sleep. Additional calibration can be performed each time a movement occurs, using the assumption that although the distribution of weight changes, the total weight of the loads does not change between times immediately before and after the movement.

Figure 4A:
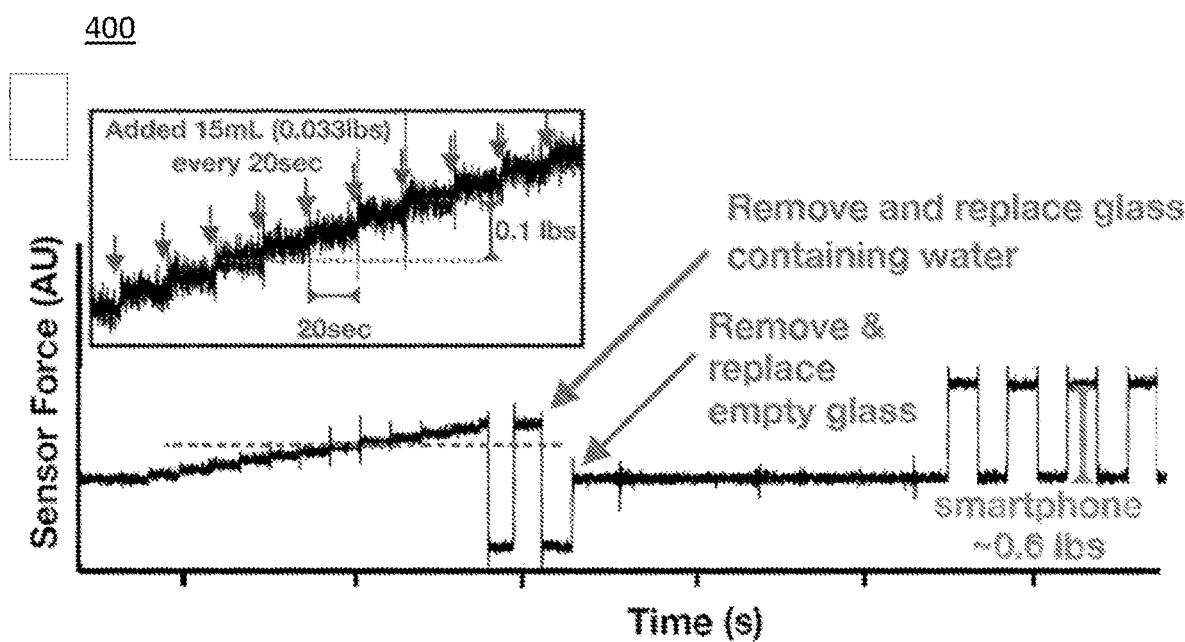
FIG. 4A-FIG. 4C illustrate sensitivity and resolution features of a health monitor system consistent with implementations of the current subject matter.
Figure 4B:
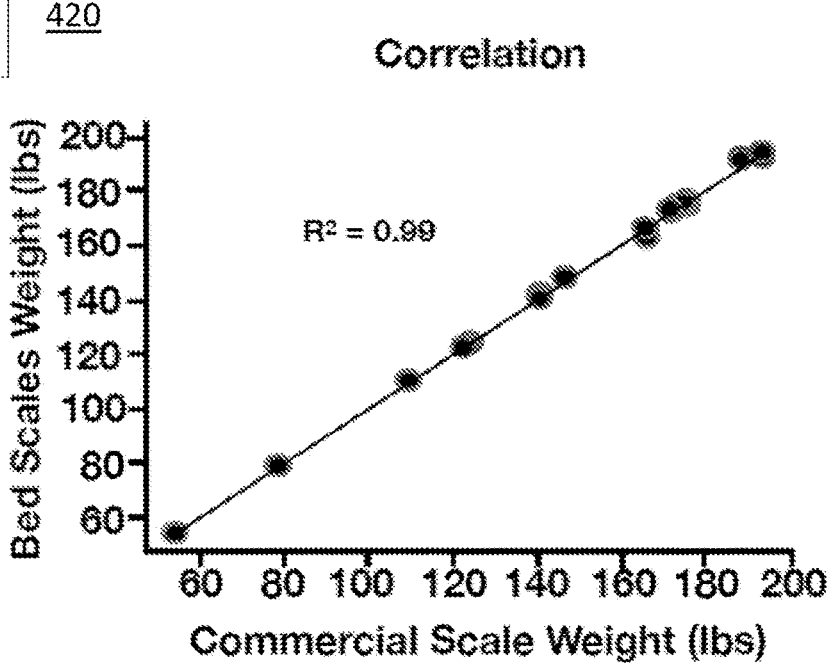
Figure 4C:
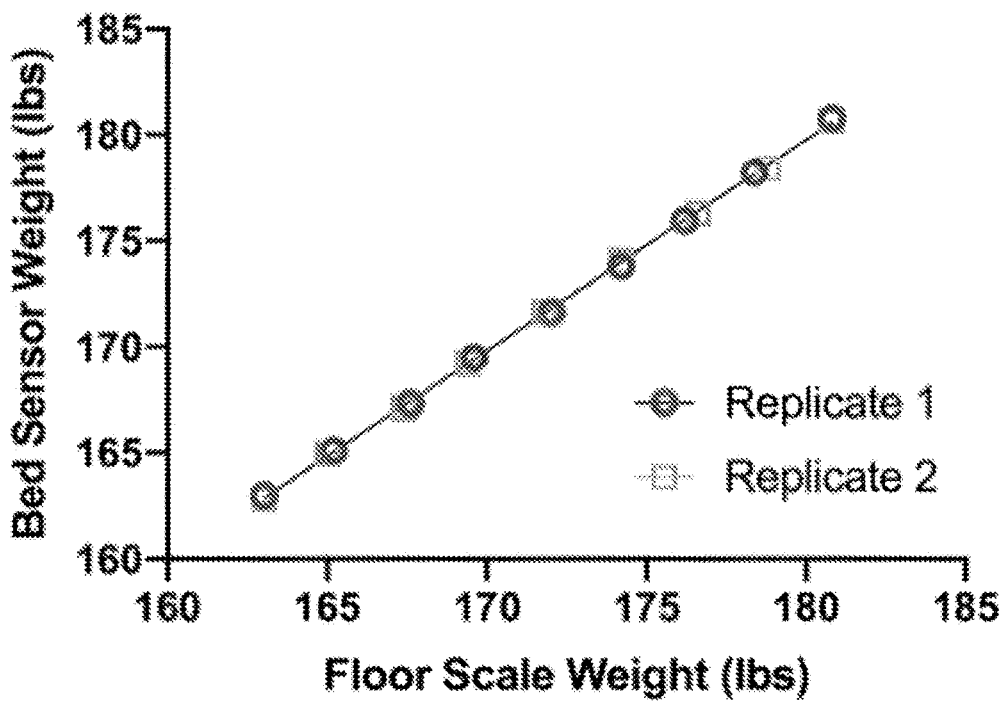

Diagram 400 of FIG. 4A, 420 of FIG. 4B, and 440 of FIG. 4C represent sensitivity and resolution features of the sensors 120 of the health monitor system 100. As an example, and as shown in FIG. 4A, 15 mL aliquots of water (0.033 pounds) were added to a bed every 20 seconds for a total of 4 minutes (180 mL, 0.396 pounds) followed by removal and replacement of the full and empty glass, and removal and placement of a smartphone (about 0.6 lbs), which are representative of small objects commonly placed on a bed. This revealed a root-mean-squared (RMS) noise to be about 0.02 pounds. For comparison, the limit of resolution of conventional bathroom scales is typically 0.2 pounds. As shown in FIG. 4B, there is a strong correlation ($R^2$=0.99, n=19) when comparing total body weight measurements of healthy volunteers using the health monitor system 100 and a commercial floor scale. The measurement of human weight changes that may be experienced during progressive volume overload was validated by comparing the sensors 120 to a commercial bathroom scale while a healthy volunteer added and removed increasingly heavy ankle weights before getting into and out of the bed. The observed result, shown in FIG. 4C, is a clear linear relationship ($R^2$=0.99).

Figure 5A:
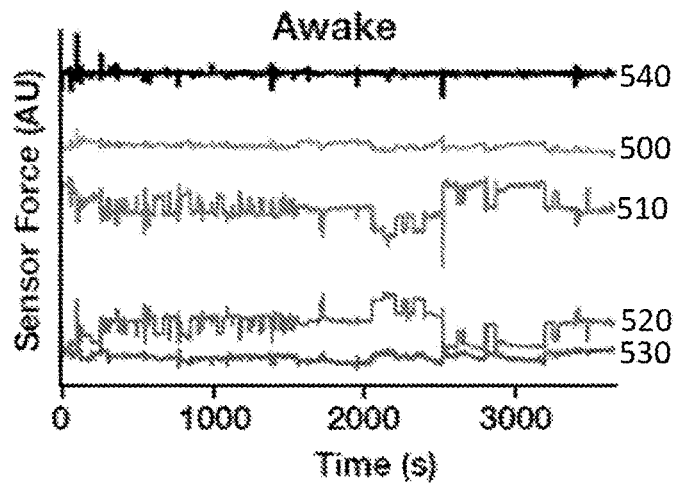
FIG. 5A-FIG. 5C illustrate weight measurement data consistent with implementations of the current subject matter.
Figure 5B:
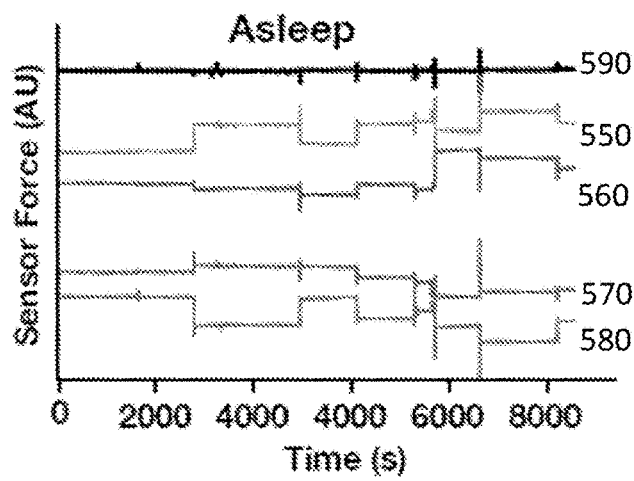
Figure 5C:
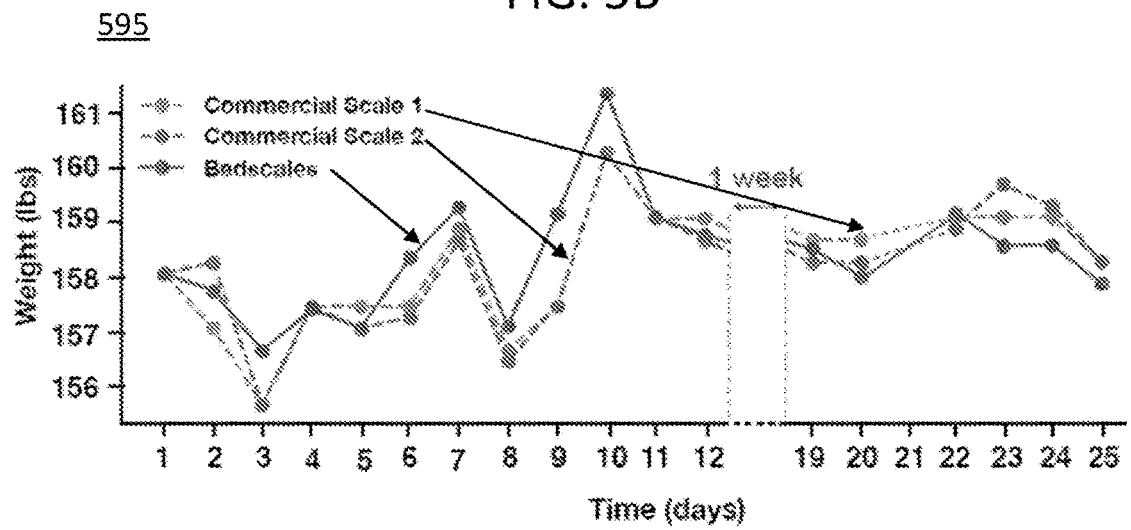

FIG. 5A and FIG. 5B illustrate measurements of the sensors 120 while a patient is awake and changing positions (FIG. 5A) and while a patient is asleep (FIG. 5B). As shown in FIG. 5A and FIG. 5B, individuals change position nearly continuously while awake but only episodically during sleep. Curves 500, 510, 520, and 530 in FIG. 5A and curves 550, 560, 570, and 580 in FIG. 5B illustrate load measured by each of the four sensors 120 positioned beneath four bed legs. The sum of the loads measured by the four sensors 120 is represented as 540 in FIG. 5A and as 590 in FIG. 5B. FIG. 5A illustrates an about 60-minute segment of data collected while the patient is in bed but awake using a laptop computer. Although the load redistributions are frequent, the total measured weight remains constant. FIG. 5B illustrates an about 3 hour recording during sleep when load redistributions are considerably less frequent. Diagram 595 of FIG. 5C provides a comparison of several weeks of daily weights measured by the sensors 120 of the health monitor system 100 compared to two commercial floor scales (each with a reported accuracy of about 0.2 pounds). As shown, errors between the sensors 120 of the health monitor system 100 and the individual commercial scales are comparable to the errors between the commercial scales.

Figure 6A:
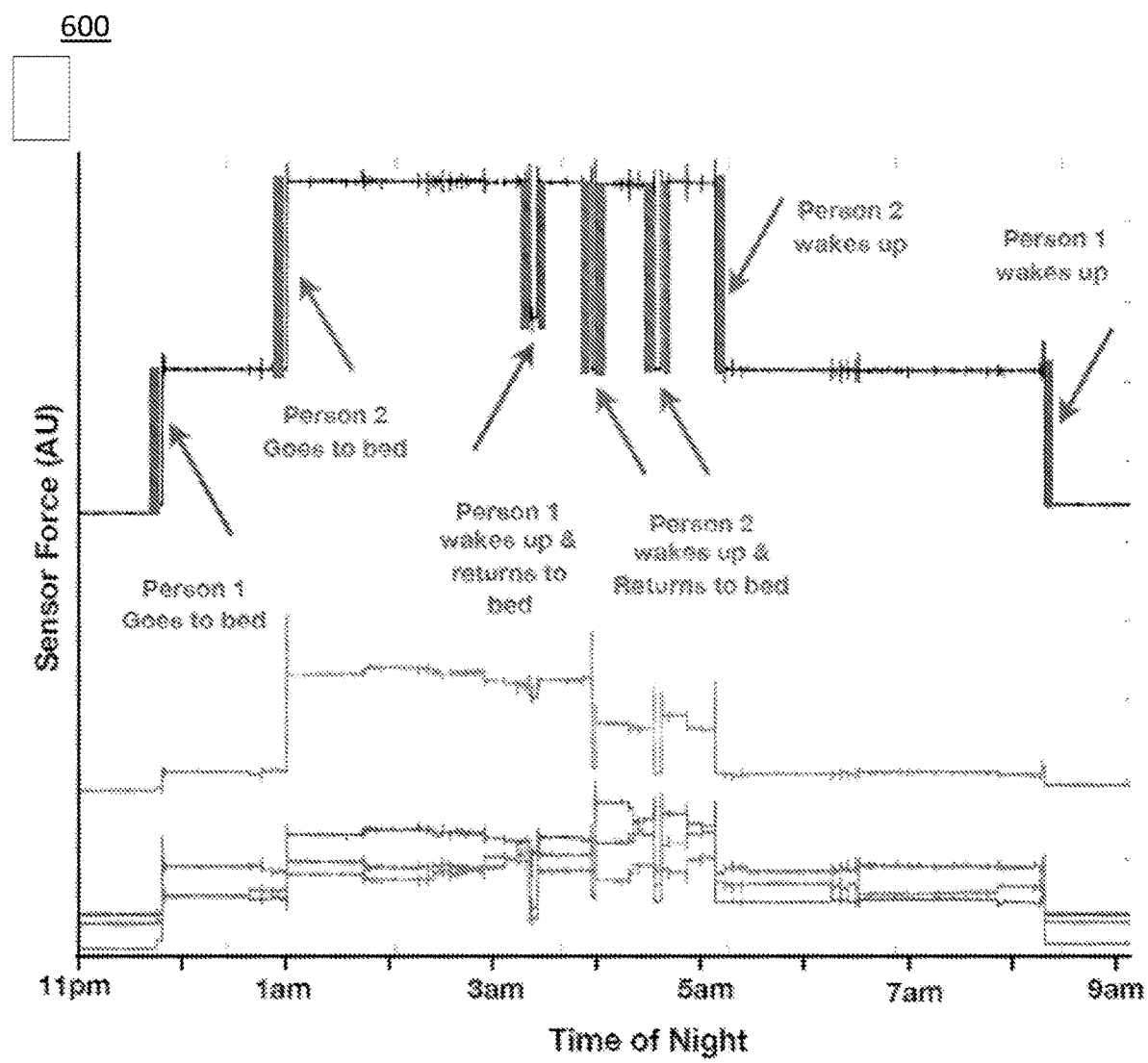
FIG. 6A-FIG. 6B illustrate aspects of demixing weight signals consistent with implementations of the current subject matter.

Implementations of the current subject matter provide for demixing force signals when the bed is shared by a partner or a pet. According to aspects of the current subject matter, weights of two or more individuals may be separately inferred based on a time delay in timing of their arrival into bed, based on the premise that individuals rarely get into bed at precisely the same time. Diagram 600 of FIG. 6A illustrates overnight measurements of two partners sharing a bed. Individual sensor tracings (indicative of the load measured by each of the four sensors 120 positioned beneath four bed legs) are provided, as is the sum of the loads measured by the four sensors 120. Diagram 600 illustrates sudden weight changes due to each person getting into and out of the bed as indicated.

Figure 6B:
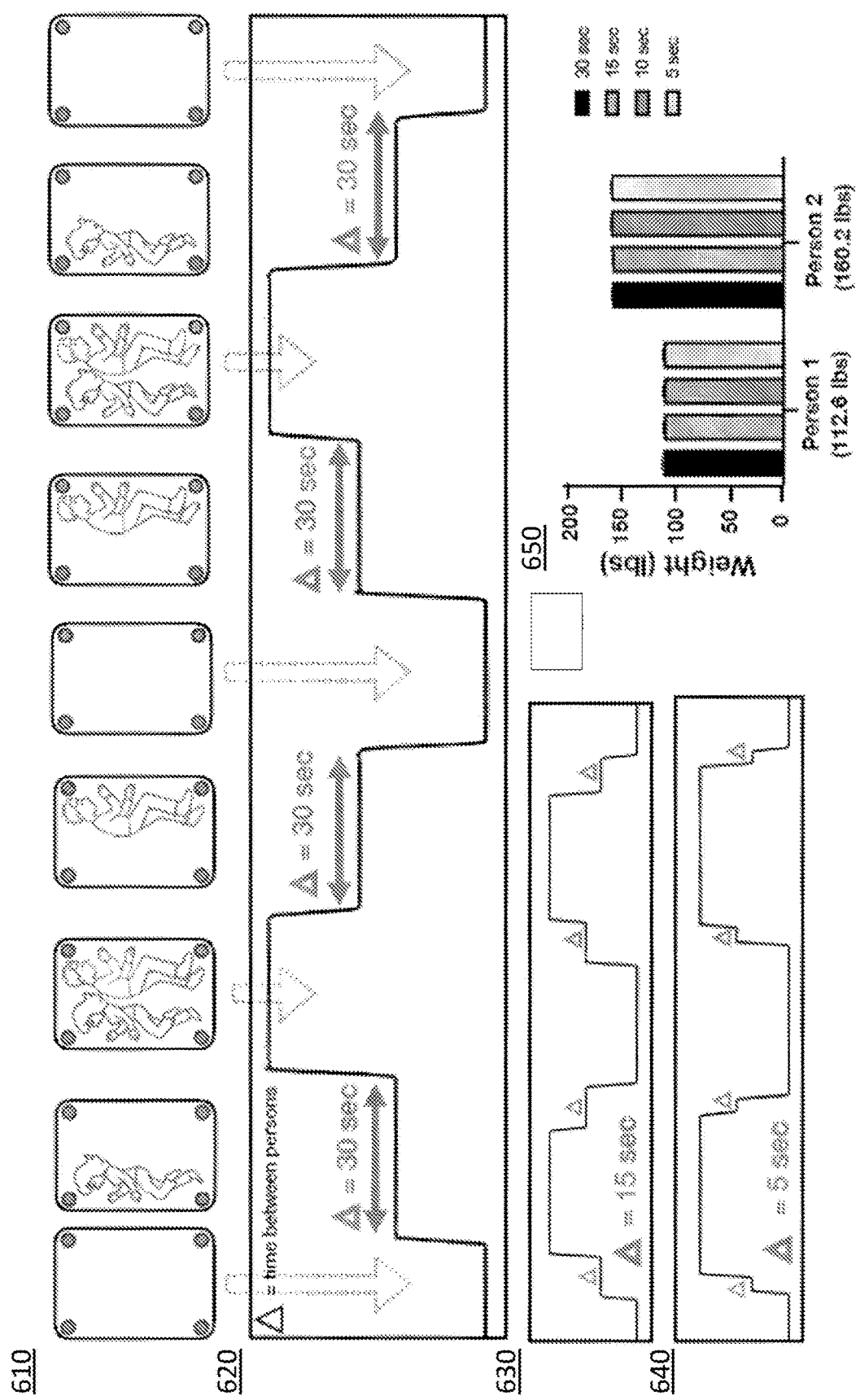

FIG. 6B illustrates determination, according to aspects of the current subject matter, of an interval that allows for discrimination of two-person weights. In particular, simultaneity tests in which two persons entered and exited the bed at successively decreasing time intervals were conducted, as represented by diagrams 610, 620, 630, and 640. As shown, when the interval was reduced from 30 seconds to 5 seconds, the two individuals were easily discriminated and reproducibly weighed (see diagram 650). Diagram 610 indicates movement and positioning of person one and person two. Diagrams 620, 630, and 640 illustrate corresponding total weight signals measured by the sensors 120 with a time interval of 30 seconds, 15 seconds, and 5 seconds, respectively. Diagram 650 illustrates estimates of decoupled weights of the two individuals for each time interval.

Figure 7A:
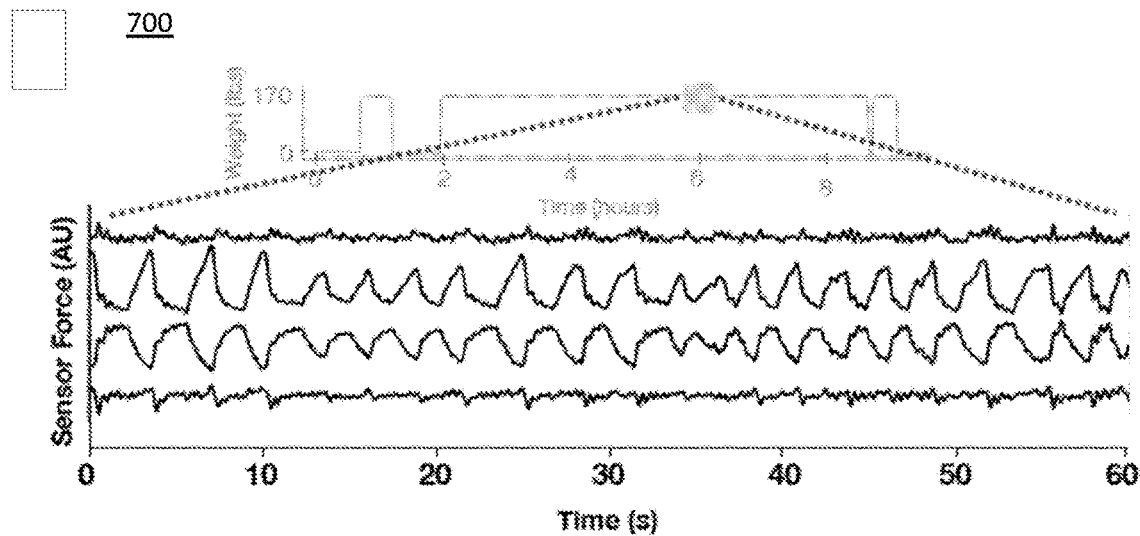
Figure 7B:
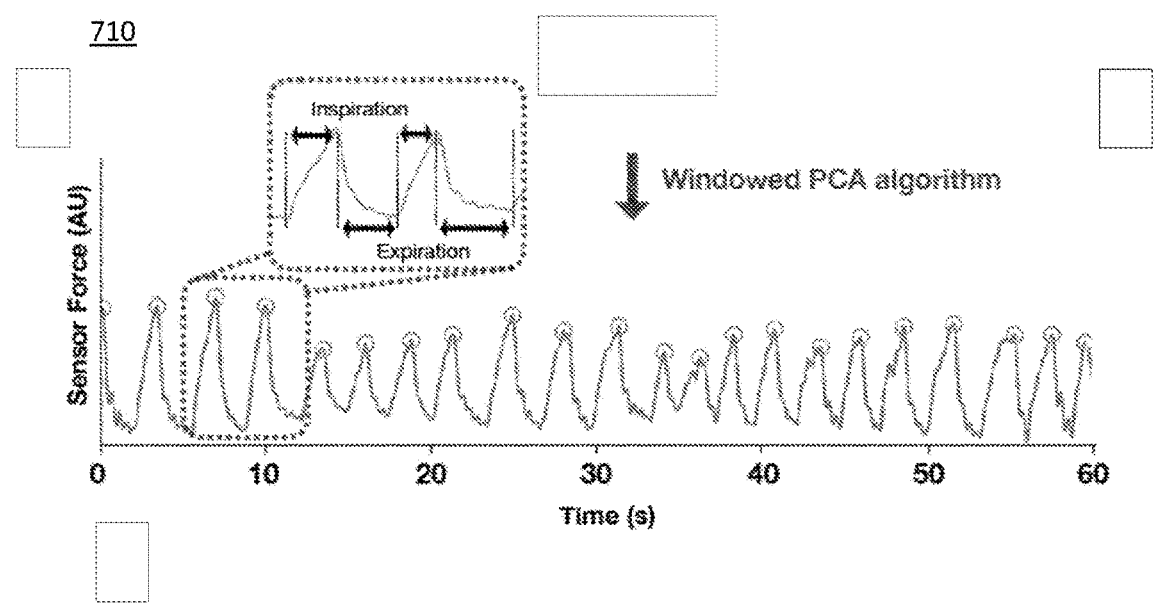

Aspects of the current subject matter provide for respiratory monitoring using data obtained from the sensors 120 of the health monitor system 100. In particular, aspects of the current subject matter take into account that when a patient is asleep in bed, episodic musculoskeletal movements are separated by comparatively long movement-free intervals during which low variance physiological signals (such as respirations and cardiac contractions) may be measured with high fidelity. That is, chest wall movements during respirations generate a detectable shift in the distribution of weight between the sensors 120 beneath each leg of the bed. In fact, as illustrated in diagram 700 of FIG. 7A, frequency-dependent filtering with cutoffs at 0.167 Hz and 1.5 Hz reveal an oscillatory signal characteristic of respirations, consistent with the redistribution of load that accompanies chest wall movement during inspiration and expiration. Consistent with implementations of the current subject matter, a single optimal respiratory signal with algorithmically-detectable peaks is created by using principle component analysis within a sliding window to calculate eigenvalues that are multiplied by individual sensor measurements and algebraically summed. The resulting signal exhibits brisk linear upstrokes consistent with inspiration, followed by longer exponential decays consistent with expiration (see diagram 710 of FIG. 7B). The resulting signal allows quantification of inspiration-expiration (I:E) ratios, which are prolonged in obstructive lung diseases such as asthma or COPD. The measurements consistent with implementations of the current subject matter were validated by comparing evolving respiratory rates as determined by the health monitor system 100 (denoted as "Bedscales" in diagram 720 of FIG. 7C) to simultaneously recorded commercial respirometry belt measurements. As shown in diagram 730 of FIG. 7D, close correlation with an $R^2$ of 0.9992 is observed. As shown in diagram 740 of FIG. 7E, Bland-Altman plots (to represent measurement error) result in a standard deviation of about 0.04 bpm.

Figure 8A:
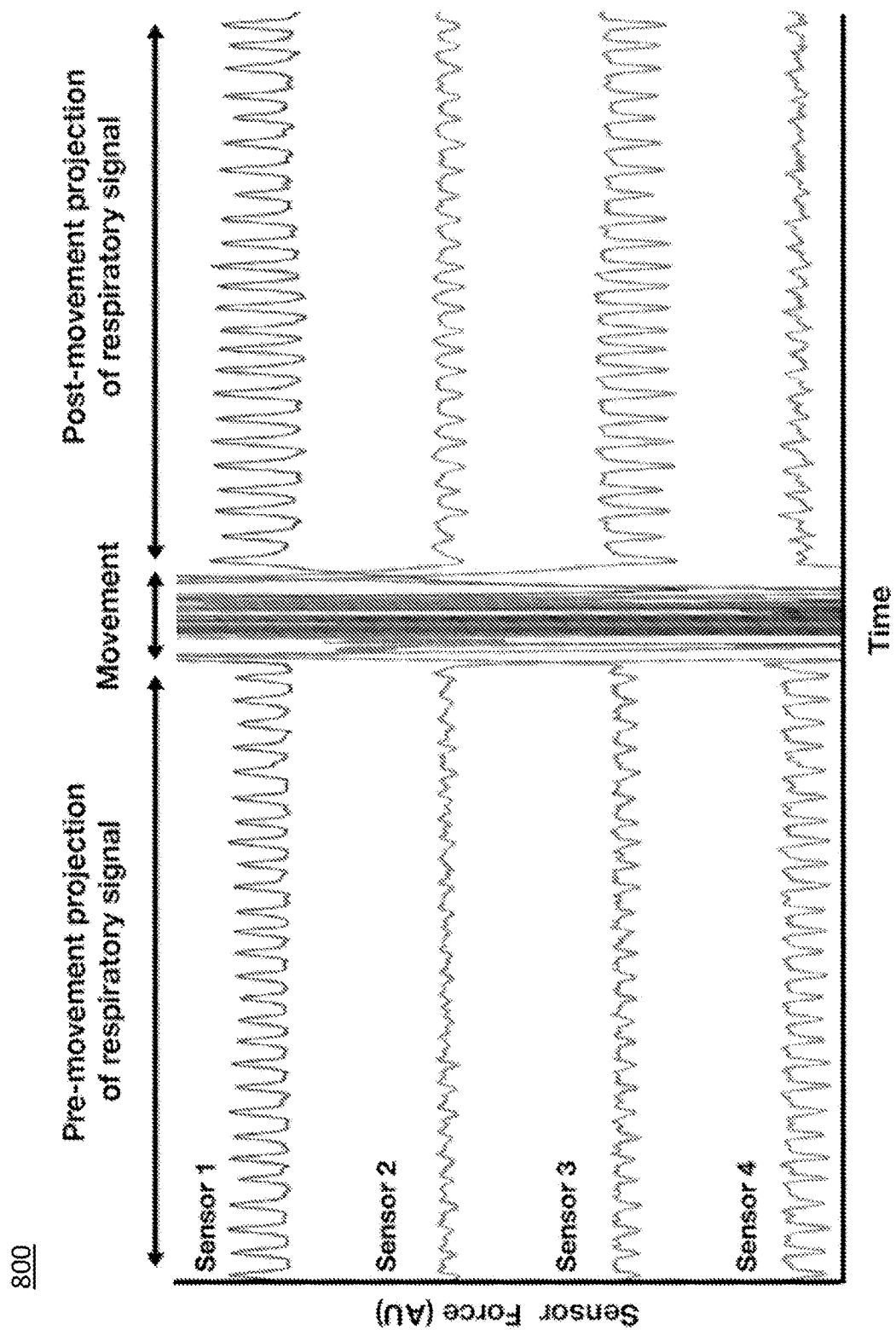

Aspects of the current subject matter provide for demixing respiratory signals when the bed is shared by a partner or pet. The respiratory signals are, consistent with implementations of the current subject matter, obtained by detecting changes in the distribution of weight between the sensors 120 beneath each leg of the bed. In particular, aspects of the current subject matter take into account that when an individual person sleeps on the bed, the magnitude of the measured respiratory signal differs between each bed leg but is consistent across time between episodic movements and is position-dependent (see diagram 800 in FIG. 8A). In particular, as shown in FIG. 8A, the relative amplitudes of respiratory signal measured by the four sensors is locally consistent but changes suddenly after a movement. This indicates that during sleep and between movements, patients can be modeled as respiratory point sources. Thus, consistent with implementations of the current subject matter, each person is modeled as a respiratory point source, allowing the respiratory signals of two individuals sharing the bed to be demixed using source separation mathematics. For example, consistent with implementations of the current subject matter, a hidden Markov model may be used with the mechanical respiratory sources interpreted as latent signals that evolve in a stochastically continuous manner and that are mixed through a linear operation with additive sensor noise to give rise to the signals at the individual detectors. Interpreting the linear operation as unknown, the expectation-maximization algorithm may be used to find the maximum-likelihood estimate. Given the maximum-likelihood estimate, a Kalman smoothing algorithm may be used to extract the mechanical respiratory patterns of the two sources.

Figure 8B:
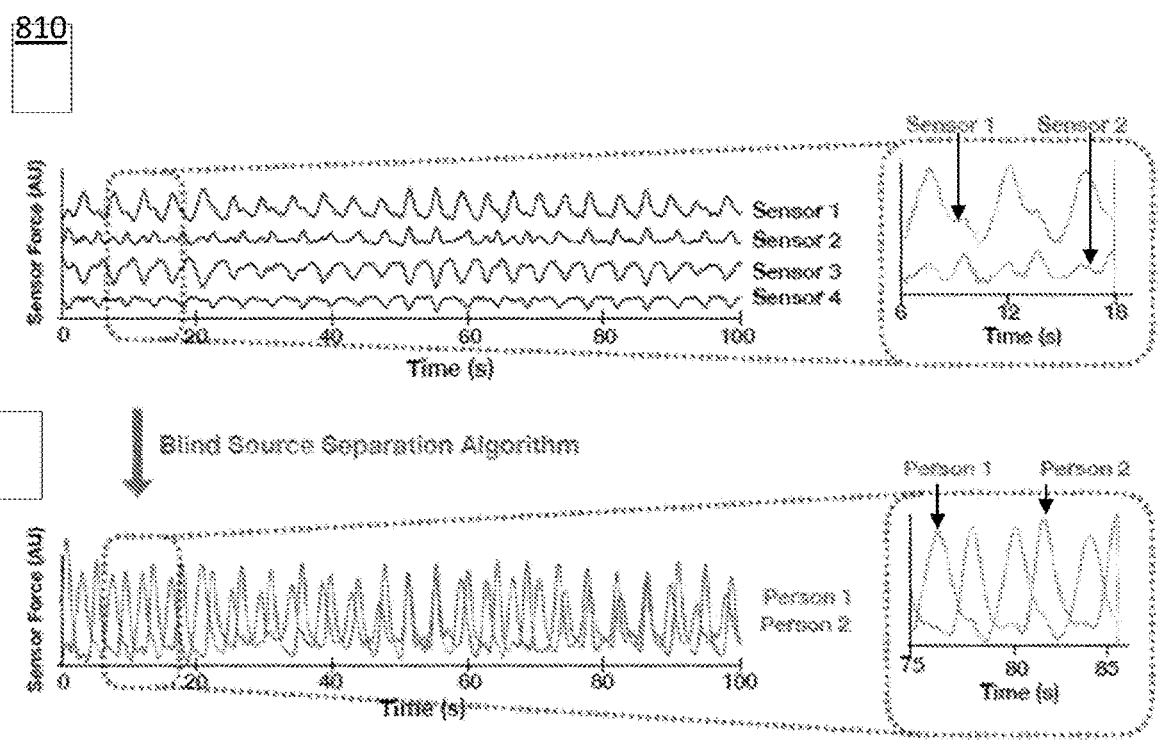

Diagram 810 of FIG. 8B illustrates that when two individuals sleep in bed at the same time, the signals from the sensors 120 beneath the legs of the bed have distinct respiratory patterns that go in and out of phase. The top inset of diagram 810 illustrates the signals from two of the sensors, each predominantly measuring one person with contaminating signal from the second person. The demixed signals for person one and person two consistent with implementations of the current subject matter are illustrated in FIG. 8B.

The demixing strategy consistent with implementations of the current subject matter was validated by measuring the signals from the sensors 120 of the health monitor system 100 for two individuals sharing the bed while simultaneously recording ground-truth respiratory signals using commercial chest belts. As illustrated in FIG. 8C-FIG. 8E (diagrams 820, 830, and 840), the demixed signals strongly correlated with those of the corresponding respiratory belt, showed minimal error when compared to the corresponding person's chest belt but a large error when compared to the opposite person's belt data.

Figure 9A:
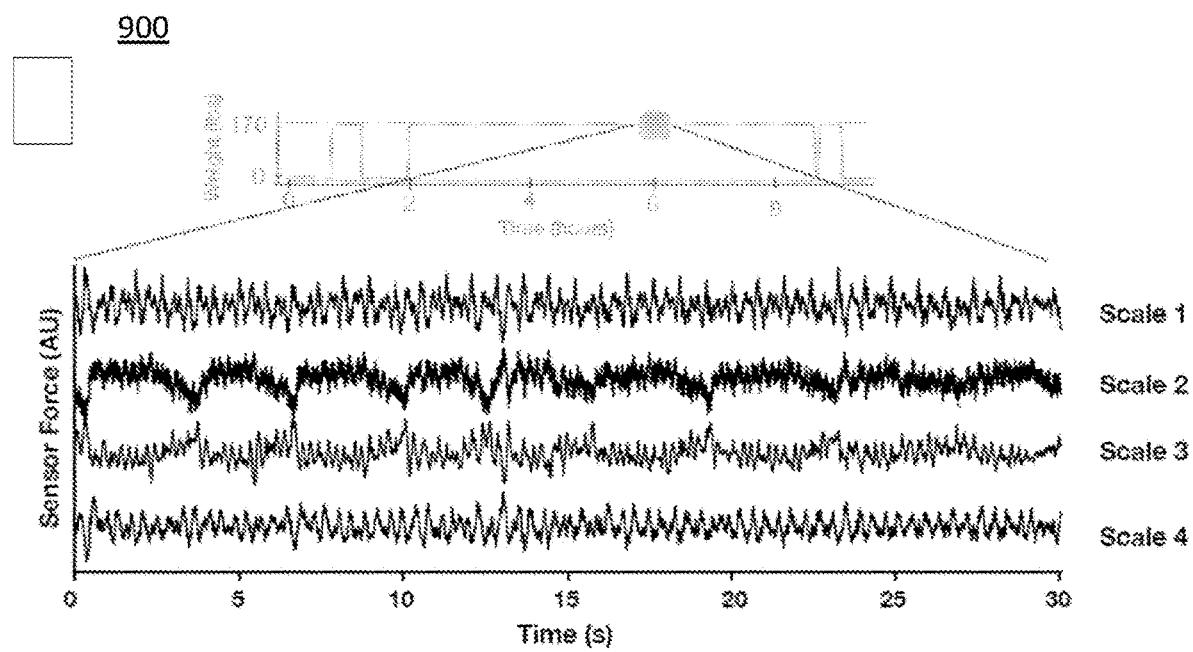
FIG. 9A-FIG. 9F illustrate aspects of ballistocardiogram monitoring consistent with implementations of the current subject matter.
Figure 9B:
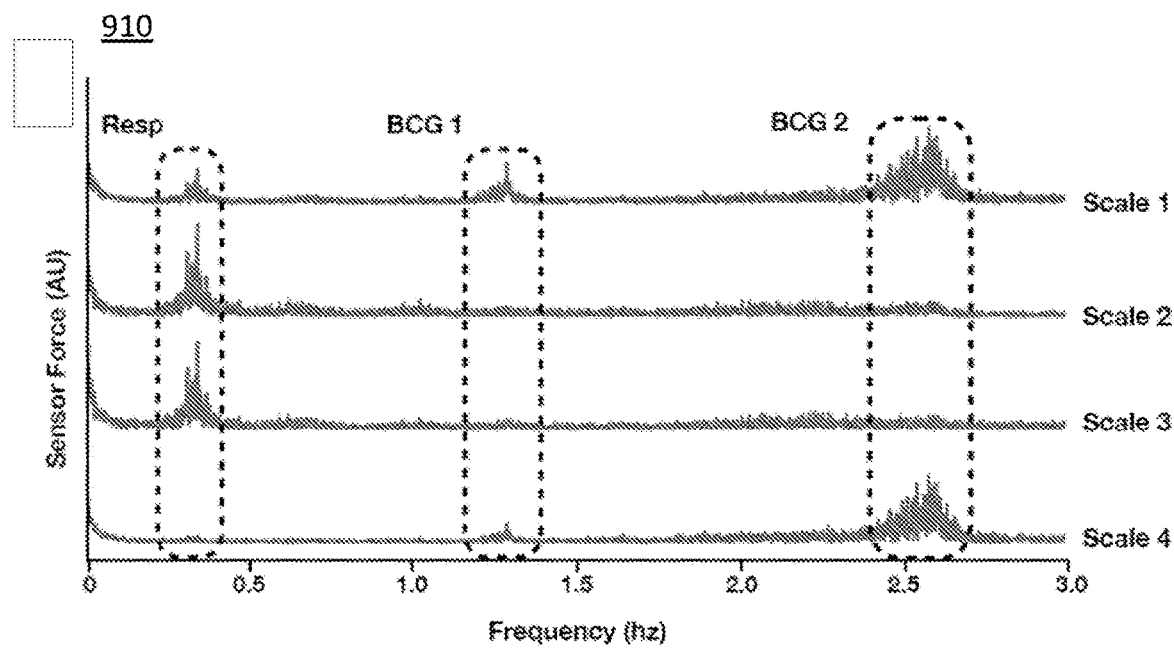
Figure 9C:
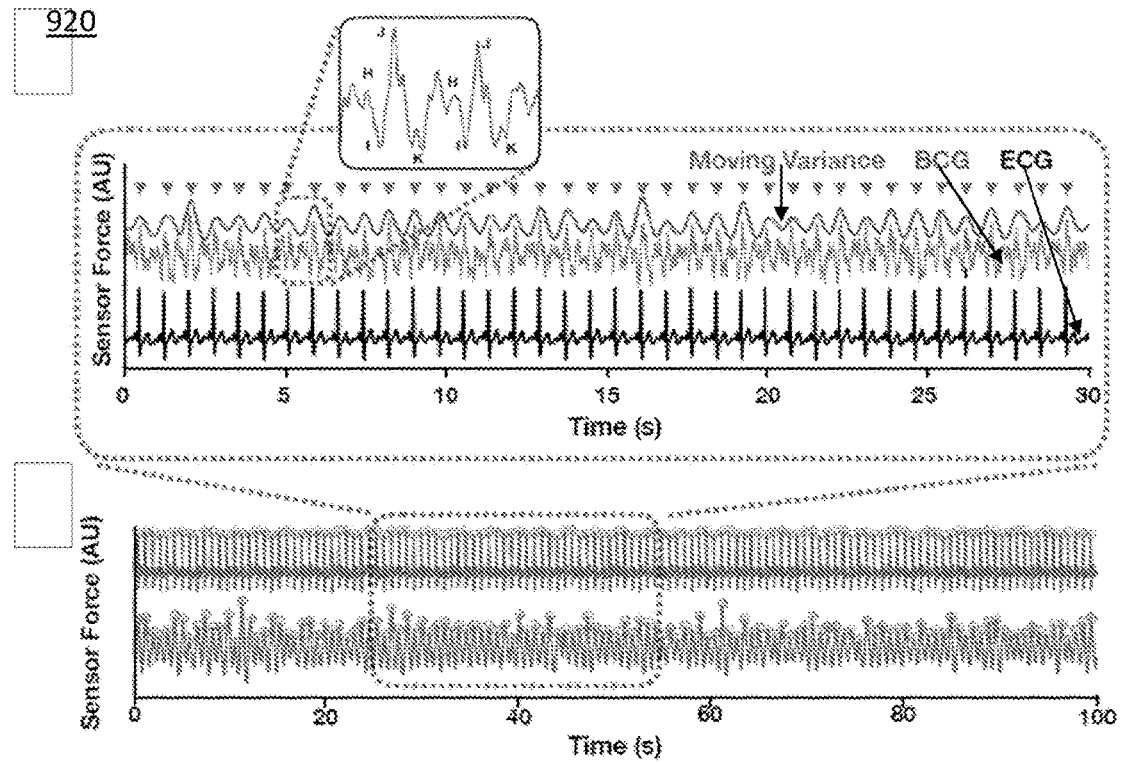

Aspects of the current subject matter provide for ballistocardiogram monitoring using data obtained from the sensors 120 of the health monitor system 100. The mechanical force of each heartbeat reverberates through the aorta leading to a characteristic signal known as the ballistocardiogram (BCG) with characteristic waves and segments representing the mechanical correlation of the electrocardiogram. Examination of the raw sensor data obtained from the sensors 120, consistent with implementations of the current subject matter, revealed the ballistocardiogram is superimposed on the respiratory signals (see 900 of FIG. 9A). Analysis of the frequency spectrum confirms that energy is concentrated in respiratory and ballistocardiogram bands (see 910 of FIG. 9B, which illustrates the frequency spectrum from each of the four legs highlighting respiratory and ballistocardiogram frequency bands and showing the distribution of energy across the four sensors 120). Using the sensor 120 with the highest ballistocardiogram energy, frequency-dependent filtering at cutoffs of 1 Hz and 50 Hz, moving variance and moving mean filtering, and a final frequency-dependent filter with cutoffs of 1 Hz and 3 Hz were performed to create a single-peaked ballistocardiogram-derived signal that spans both normal and elevated heart rates (see 920 of FIG. 9C). This allows longitudinal adherence-independent monitoring of cardiac rate and regularity and allowed inference of relative cardiac ejection forces. Diagram 920 of FIG. 9C illustrates a single-peak ballistocardiogram signal with annotation of peaks derived from frequency-dependent, moving variance, and moving mean filtering of the underlying ballistocardiogram. The inset in FIG. 9C illustrates annotation of the characteristic ballistocardiogram peaks. The corresponding ground truth electrocardiogram is also shown.

Figure 9D:
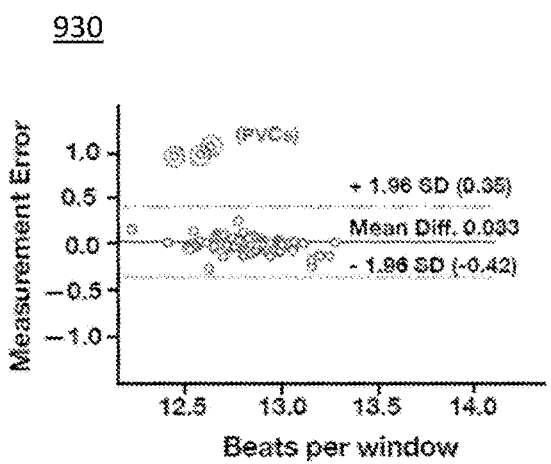
Figure 9E:
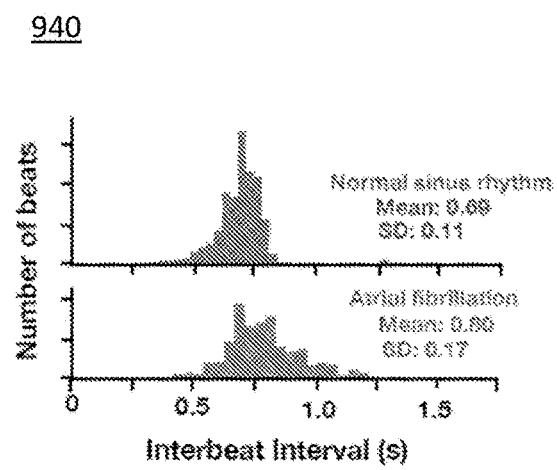
Figure 9F:
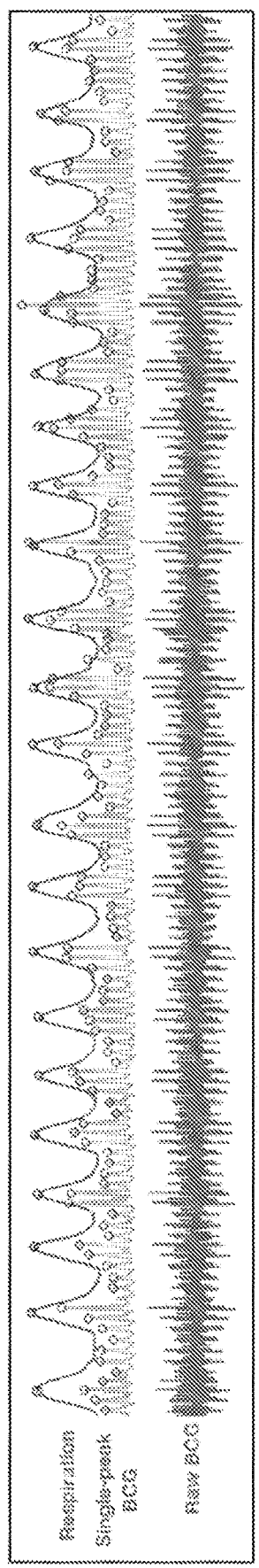

Consistent with implementations of the current subject matter, the health monitor system 100 heart rate estimations were validated by comparing to simultaneously recorded electrocardiograms over 15 minutes. Bland-Altman plots reveals close quantitative agreement between the health monitor system 100 and ECG (SD=0.9 bpm) (see 930 of FIG. 9D). Quantification of inter-beat interval variability allows discrimination of patients with atrial fibrillation (SD=0.17 seconds) and normal sinus rhythm (SD=0.11 seconds) (see 940 of FIG. 9E). Since respirations are known to alter stroke volume via changes in intrathoracic pressure, the magnitude of the single-peak BCG signal as a function of respiratory phase was examined. Indeed, the ratio of the inspiratory to expiratory single-peak BCG amplitude was systematically greater than 1, indicating respirophasic stroke volume variation resulting from cardiopulmonary coupling (see 950 of FIG. 9F). Diagram 950 illustrates the relationship between respiratory signals and single-peak ballistocardiogram signals with underlying ballistocardiogram signals, illustrating respirophasic variation is ballistocardiogram amplitude.

Figure 10:
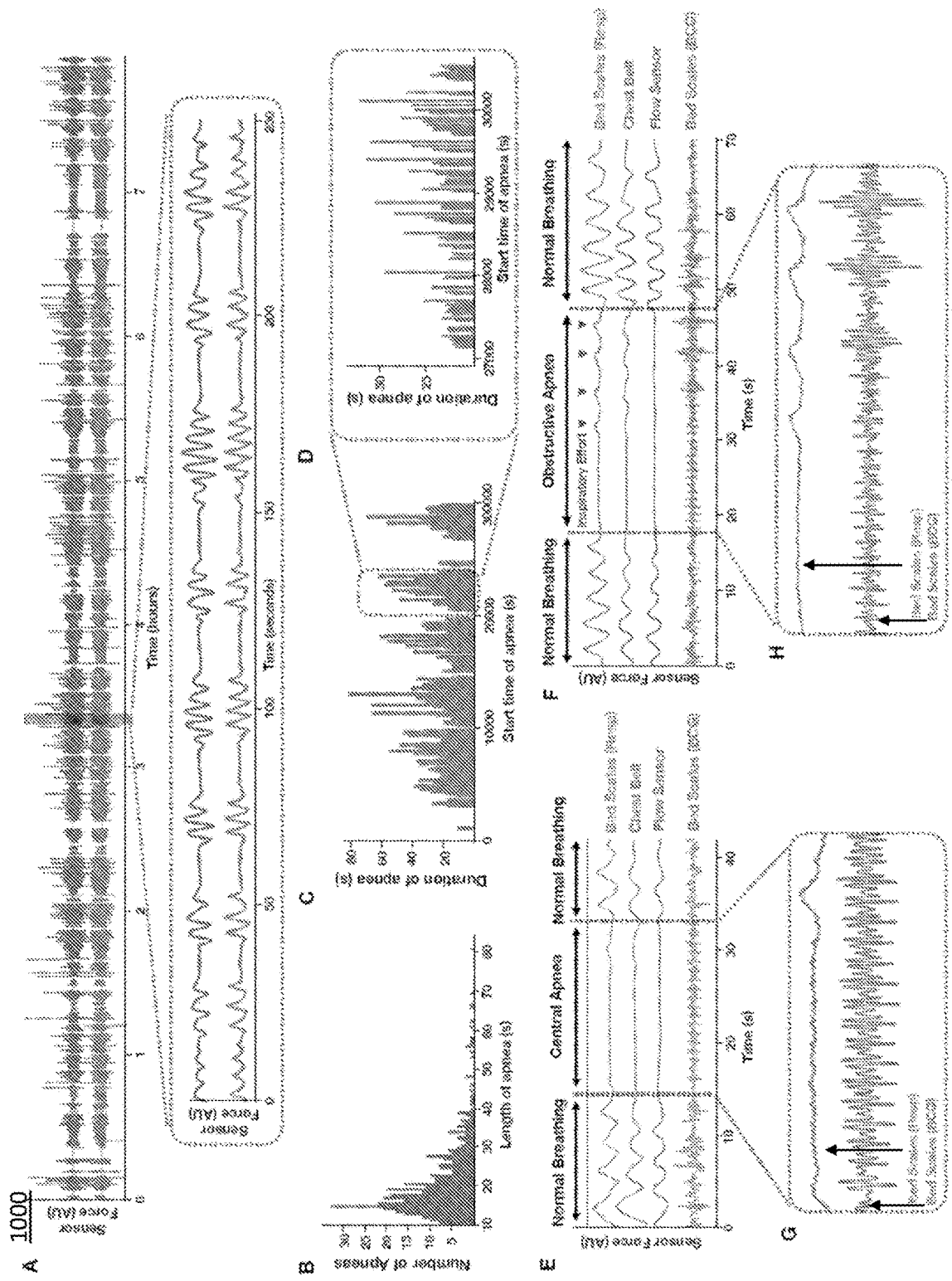
FIG. 10 illustrates aspects of an example sleep study and apnea monitoring consistent with implementations of the current subject matter.

With reference to diagram 1000 of FIG. 10, the health monitor system 100 according to aspects of the current subject matter was used to measure pathologic respirations from an individual who had a high burden of central and obstructive sleep apneas (OSA and CSA) (A of FIG. 10). OSA is characterized by anatomical airway obstruction despite ongoing respiratory effort, whereas CSA is characterized by repetitive cessation of respiratory air flow during sleep due to lack of ventilatory effort; both are common in patients with heart failure. During the about 8-hour study, respiratory signals were measured utilizing the health monitor system 100, along with the more cumbersome chest and abdomen belts and nasal pressure transducers used as airflow monitors. Data was aligned and registered to adjust for differences in sampling frequencies, and the distribution of inter-breath intervals greater than 10 seconds were defined as apneas (B of FIG. 10). No flow was detected during 407 apnea episodes with mean duration of 22 seconds, a standard deviation of 10.5 seconds, and a maximum apnea duration of 81 seconds. The distribution of apneas was periodic with 5 apnea-dense clusters separated by apnea-free intervals (C of FIG. 10). Within each apnea cluster, substructure was observed during which the longest apneas were followed by the longest apnea-free periods (D of FIG, 10). Close examination of the tracings demonstrates that the health monitor system 100 consistent with implementations of the current subject matter discriminates obstructive and central apneas based on the presence of low amplitude unproductive respiratory efforts (obstructive) or the absence of effort (central) (E and F of FIG. 10). Examination of simultaneous ballistocardiograms showed stable amplitude signals in the absence of respiratory effort followed by transient increases in ballistocardiogram amplitude following the strong negative intrathoracic pressure, providing a new tool with which to investigate beat-by-beat hemodynamic consequences of central and obstructive apneas (G and H of FIG. 10). Taken together, these data demonstrate that the health monitor system 100 consistent with implementations of the current subject matter can perform high fidelity monitoring of normal and pathologic respiratory dynamics and their hemodynamic consequences without the need for obtrusive adherence-dependent sensors and may allow longitudinal characterization of recently reported night-to-night variability.

Figure 11:
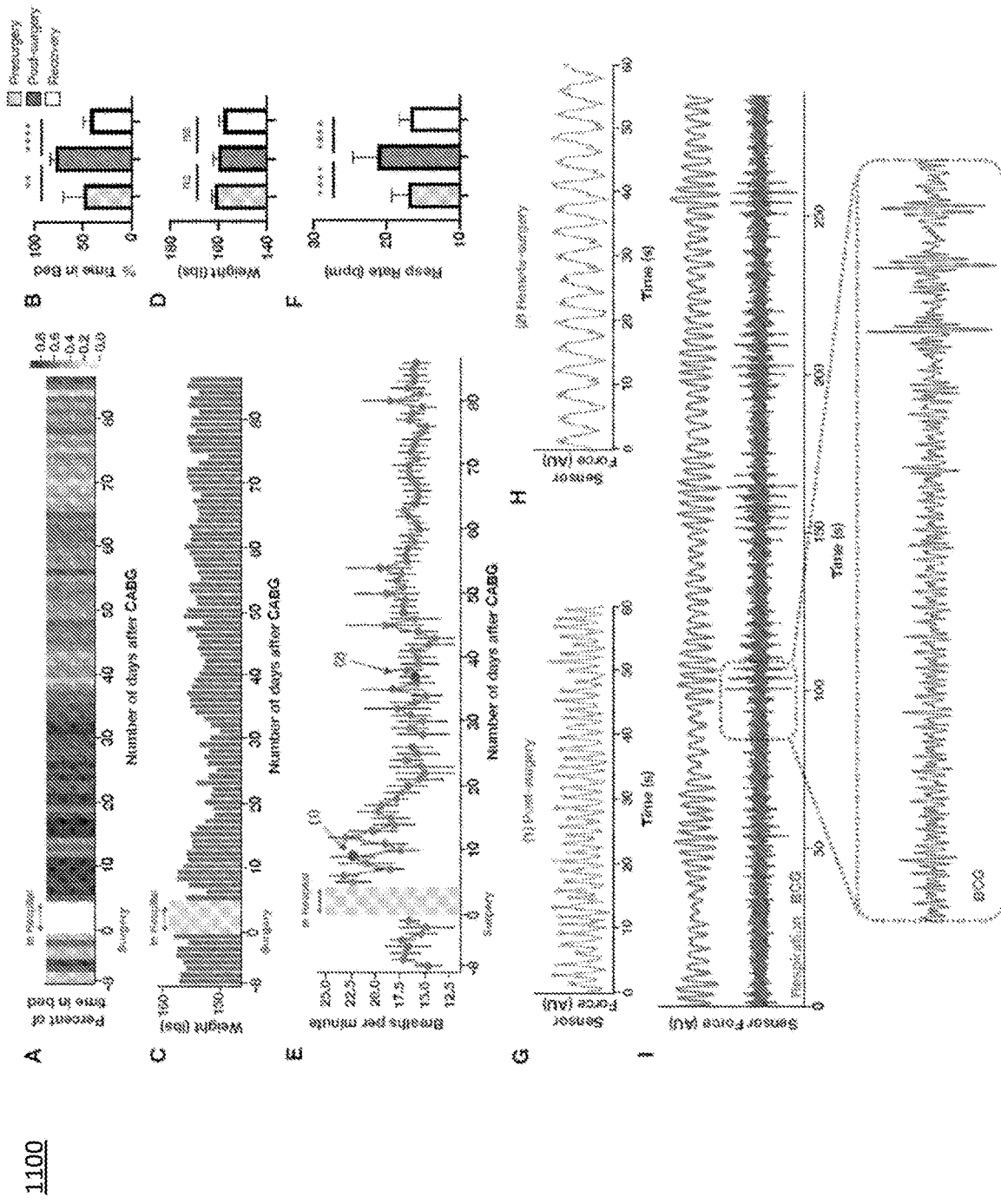
FIG. 11 illustrates aspects of an example long-term in-home monitoring scenarios consistent with implementations of the current subject matter.

With reference to diagram 1100 of FIG. 11, the health monitor system 100 according to aspects of the current subject matter was used to evaluate real-world utility. In particular, three months of in-home continuous monitoring was performed for a 61-year-old male patient with newly discovered heart failure (EF 15%) who was found to have multivessel coronary artery disease requiring coronary artery bypass surgery (CABG). After being discharged from the hospital, the health monitor system 100 was installed under his home recliner, where he slept each night. The percent time spent in the recliner each day, which ranged 40-60% before surgery, was 0% during his surgical hospitalization, and was significantly increased to about 80% for a month before gradually declining to his baseline around the same time he began attending cardiac rehab (A and B of FIG. 11). Although the patient's weight fluctuated during the 3 months, it did not show large excursions and he was felt to be euvolemic at clinic visits during the 3 months (C and D of FIG. 11). His respiratory rate trends were locally stable but exhibited gradual changes over weeks (E of FIG. 11). Compared to "pre-surgery" respiratory rates of 16-18 bpm, his "post-surgery" respiratory rates were significantly elevated, with an average of 25 bpm punctuated by frequent episodes of more extreme tachypnea (30-40 bpm) (E, F, and G of FIG. 11). His respiratory rate gradually decreased over 2-3 weeks following surgery and stabilized near his baseline respiratory rate of 18 bpm, consistent with previously reported respiratory rate recovery times following cardiac surgery (E, F, and H of FIG. 11). Although his ventricular function modestly improved from 15% to 25%, it remained severely depressed. Consistent with his persistent ischemic cardiomyopathy, was his high burden of periodic breathing (periodicity of >30 seconds) and low amplitude nadirs along the spectrum of heart-failure-associated Cheyne-Stokes Breathing (I of FIG. 11). This suggests the health monitor system 100 consistent with implementations of the current subject matter may enable screening for sleep disordered breathing and provide longitudinal data about relationships between changes in nocturnal breathing and cardiovascular function. Since development of CSA corresponds to paroxysmal nocturnal dyspnea, the health monitor system 100 may also improve detection of heart failure symptoms, as this often goes unrecognized by patients and unreported to physicians. Throughout the in-home studies, patients reported no concerns and reported being unaware of the sensors.

Figure 12A:
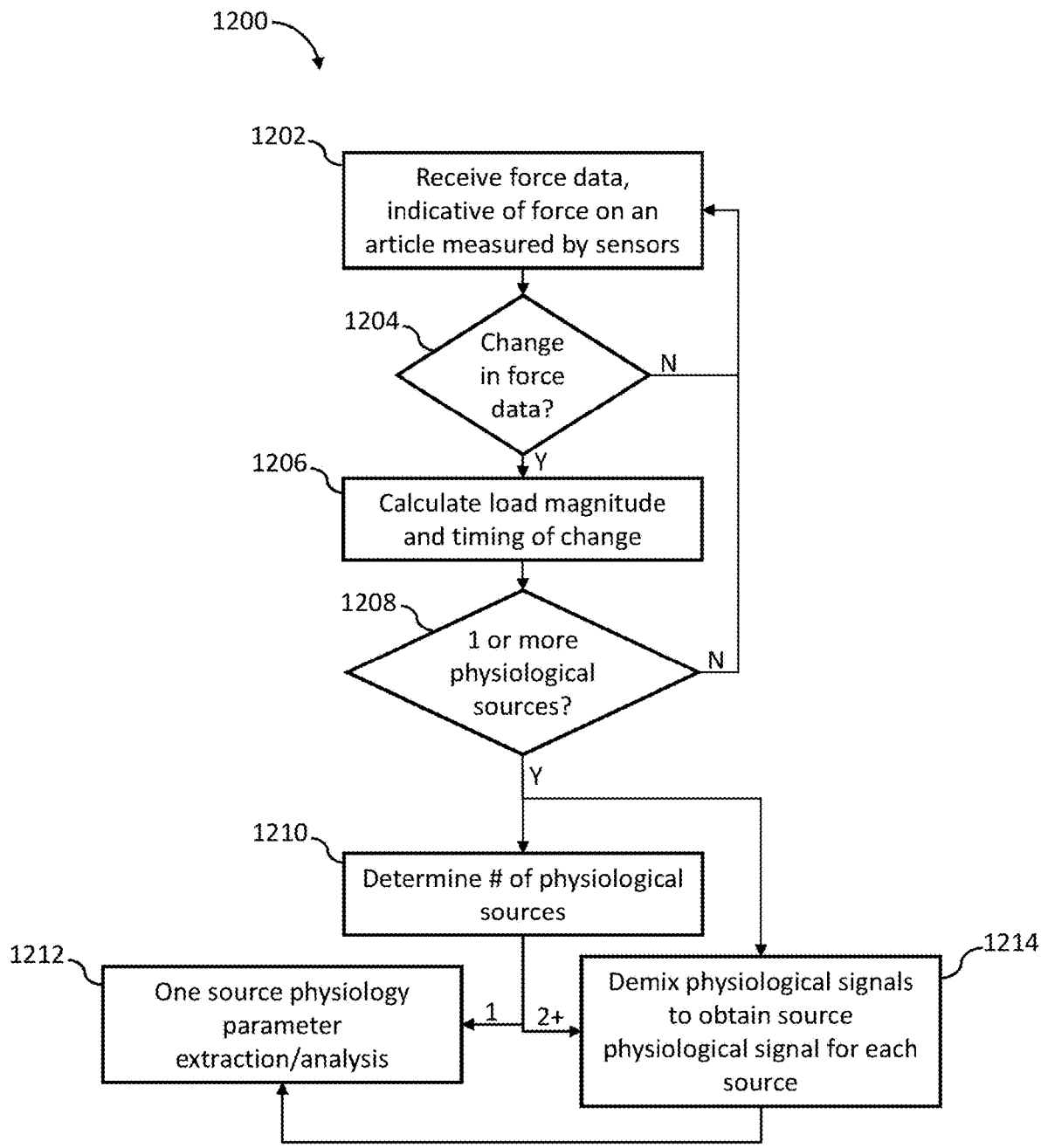
FIG. 12A depicts a flowchart illustrating a process consistent with implementations of the current subject matter.

FIG. 12A depicts a flowchart 1200 illustrating an example process consistent with implementations of the current subject matter.

At 1202, force data from the plurality of sensors 120 is received. For example, the remote processing device 130 may receive force data, as measured from the plurality of sensors 120, from the communication module 110. With reference to FIG. 1A, consistent with implementations of the current subject matter, the sensors 120 are configured to engage with a member of an article on which a first user (which may be a person or an animal) is positioned. For example, the sensors 120 may be positioned beneath respective legs of a bed on which the first user is resting or sleeping. According to aspects of the current subject matter, each of the sensors 120 is configured to obtain force data. For example, the sensors 120 may each include force-sensing strain gauges configured in a Wheatstone bridge circuit. The sensors 120 may include a housing with a spring mechanism and a rigid bottom plate, as shown in FIG. 2A, FIG. 2B, and FIG. 2E. The sensors 120 are in communication with the communication module 110. For example, a micro-USB connection may be established between the sensors 120 and the communication module 110. Consistent with implementations of the current subject matter, the force data may be continuously sent to the communication module 110, and the force data may be continuously sent from the communication module 110 to the remote processing device 130. According to some aspects of the current subject matter, the communication module 110 may perform some processing (e.g., local signal conditioning to, e.g., de-trend, de-spike, de-noise, or the like the data) of the force data prior to transmission to the remote processing device 130.

At 1204, a determination is made, based on monitoring the force data, as to whether a change in the force data has occurred. Consistent with implementations of the current subject matter, the force data may be continuously monitored to detect changes in the force data to, for example, determine if an object (e.g., another person, a pet, an inanimate object such as a phone or book or the like) has been placed on or removed from the article. If the force data has not changed, the process continues to receive (at 1202) the force data from the sensors 120 and monitor the force data to determine (at 1204) if changes to the force data have occurred. A change in the force data may indicate an addition or removal of a person or a pet if, consistent with implementations of the current subject matter, the change in the force data is greater than a predefined threshold value. For example, the predefined threshold value may be defined such that addition or removal of a small object (e.g., a magazine) does not register as a change.

The statistics of the force across time are used, consistent with implementations of the current subject matter, to discriminate transient force changes from durable changes in load that represent added or removed objects. Analysis of the statistics of force across time also allows the weight of a person to be determined when it is applied gradually, for example if it is partially applied by a person sitting or leaning on the edge of the bed for a period of time before fully getting into the bed and adding their entire weight to the article. By analyzing the statistics of the measured forces across time, loads that are stable across specified thresholds of time may be identified and interpreted as objects. Thus, according to aspects of the current subject matter, the force data may be monitored to determine if the change in the force data is greater than a predefined threshold value for a predefined duration threshold. Such monitoring provides for determining if the loads are on the article for a sustained duration and allows for rejecting a high magnitude transient signal at the time of an object getting positioned on the article. Such monitoring also addresses the problem of a person sitting on the side of the article (e.g., a partial load) and then eventually being fully positioned on the bed. In that case, the force is less than the full weight of the person and highly variable while sitting or leaning against the article. Thus, consistent with implementations of the current subject matter, by monitoring the force data to determine if the force data changes by the predefined threshold value for the predefined duration threshold, loads that are sustained across significant times (e.g., an amount of time during which the user's physiological signals can be obtained with sufficient data for analyzing the physiological signals) are analyzed.

At 1206, following a determination at 1204 of a change in force data, the load magnitude and timing of the change may be calculated and recorded. For example, the load magnitude may be used to determine the weight of the object removed or added, and the time may be used to monitor and track length of time at which an object is on the article. When a new object is determined to be added to the article, the new object may be associated with a unique identifier by the remote processing device 130 such that details related to the new object may be tracked and recorded (e.g., by association with the unique identifier). For example, the time at which the new object is positioned on the article may be recorded, and a subsequent time when the new object is removed from the article may also be recorded (e.g., by determining that the force data has changed by an amount equal to the weight of the new object). Consistent with implementations of the current subject matter, the objects may also be classified, and the classification may be associated with the unique identifier of the object. The classification may be based on historical data and/or characteristics of the data of the object (e.g., the weight, the amount of time on and off the article, or the like).

At 1208, a determination is made by the remote processing device 130 if one or more physiological sources (e.g., living creatures such as a person or a pet) are on the article. For example, a change in the force data may not be caused by addition of a physiological source but may be caused by placement or removal of an object such as a laptop or other object that may be placed on the article. By examining the physiological signals that result from the force data, a determination may be made as to whether one or more physiological sources are on the article. For example, if it is known that one physiological source was previously on the article, and if the force data changes to signify an addition of a new object, the resulting physiological signals may be examined to determine if there is more than one physiological source on the object. As another example, the change in the force data may result from one person leaving the article. Thus, at 1208, consistent with implementations of the current subject matter, the physiological signals that result from the force data are examined to determine if one or more physiological sources are on the article. If there are not one or more physiological sources on the article, then the process may continue to 1202 to receive force data and to 1204 to monitor the force data to identify changes.

As 1210, following the determination that one or more physiological sources are on the article, the number of physiological sources may be determined. As discussed herein, such a determination may be based on previous knowledge of the number of physiological sources on the article prior to the detection of the change in the force data. Additionally and/or alternatively, the determination of the number of physiological sources may be based on an analysis of the physiological signals resulting from the received force data.

At 1212, if there is one physiological source on the article, physiology parameter extraction and analysis may be done, for example by the remote processing device 130. Consistent with implementations of the current subject matter, an amount of time on the article by the one physiological source may be based on transitions on and off the article, where the transitions are tracked by monitoring alterations in the force data. Movement by the one physiological source may also be determined. The movement may be tracked by monitoring signal variance and/or amplitude of the force data. Consistent with implementations of the current subject matter, the movements may be classified into categories and/or types based on the signal variance and/or the amplitude of the force data.

Person-specific attributes of the dynamic physiological signals (e.g., respiratory, ballistocardiogram, or movement amplitude, frequency, signal contour, apneas, periodic breathing, etc.), according to aspects of the current subject matter provide for discriminating/demixing, and may also be used to classify the physiological sources and track which physiological signals belong to which weights (which in turn may be associated with identity). By using the times at which there are changes in the number of sources, the loss or addition of these characteristic dynamic physiological signals may be connected to associated static weights and identities. This classification estimation problem may use the raw signals or the derived parameters and may be solved explicitly or by using, for example, supervised or unsupervised machine learning.

Consistent with implementations of the current subject matter, the physiology parameter extraction and analysis may also include transforming the force data of the one physiological source into physiological signals. For example, the force data may be time-domain or frequency-domain filtered to obtain respiratory signals of the one physiological source. One or more respiratory signals may be used, or a composite signal from the linear combination of some or all of the sensor signals may be created using, for example, weighting factors derived from, for example, analyses such as principle component analysis and the eigenvalues of the covariance matrix. From the respiratory signals, various respiratory parameters may be obtained and/or identified, such as respiratory peaks and valleys, inspiration/expiration phase, respiration amplitudes, inter-breath intervals, respiratory rates, rapid shallow breathing index (RSBI) (based on rate and amplitude parameters), tachypneas (e.g., frequency and duration of episodes, respiratory rates during episodes), apneas (e.g., timing duration and obstructive versus central), periodic breathing (frequencies, amplitude, duration), and the like.

Consistent with implementations of the current subject matter, the physiology parameter extraction and analysis may also include transforming the force data of the one physiological source into ballistocardiogram signals. For example, the force data may be time-domain or frequency-domain filtered to obtain ballistocardiogram signals of the one physiological source. One or more ballistocardiogram signals may be used, or a composite signal from phase-shifted and/or linearly combined sensor signals may be created using, for example, weighting factors derived from, for example, analyses such as principle component analysis and the eigenvalues of the covariance matrix. From the ballistocardiogram signals, various ballistocardiogram parameters may be obtained and/or identified, such as ballistocardiogram peaks and valleys (e.g., by creating a single-peak ballistocardiogram using moving variance and moving mean), inter-beat intervals, heart rate, beat strength from ballistocardiogram amplitudes, heart beat regularity, atrial fibrillation estimation (e.g., based on degree and duration of irregular inter-beat intervals), tachycardias (e.g., rate, duration, frequency), bradycardias and heart blocks (e.g., rate, duration, frequency), respirophasic variation (e.g., amplitudes and frequencies), and the like.

With continued reference to FIG. 12A, at 1214, if it is determined at 1210 that there are two or more physiological sources on the articles, the physiological signals resulting from the force data are demixed (or separated) to obtain a source physiological signal for each individual physiological source. Consistent with implementations of the current subject matter, the demixing (to determine, based on the plurality of physiological signals from the sensors 120, the source physiological signal for each of the individual physiological sources) includes separating into components each of the plurality of physiological signals and compositing the separated components. The components correspond to each of the plurality of physiological sources at each of the plurality of sensors 120, and the compositing forms the source physiological signal for each of the plurality of physiological sources. According to some aspects of the current subject matter, a model for each of the physiological sources may be created. Each model includes the components, where the components define a contribution of a respective physiological source to each of the plurality of physiological sources. According to some aspects of the current subject matter, to demix the physiological signals resulting from the force data, force data from at least two of the sensors 120 is used in the demixing operations. Following the demixing or separating of the physiological signals (resulting from the force data) into the source physiological signals, the process may proceed to 1212 for parameter extraction and analysis.

Consistent with implementations of the current subject matter, the number of physiological sources does not need to be known prior to the demixing operation (e.g., at 1214). For example, the physiological signal resulting from the force data of one person may be demixed, resulting in the source physiological signal of the one person as well as, for example, noise sources. As an example, if there is one person on a bed but parameters are fit assuming there are four sources, the demixing operation consistent with implementations of the current subject matter identifies one physiological source and three noise signals. If there are two people on the bed, demixing results in two physiological sources and two noise sources. If there is one pet and two people on the bed, then demixing yields three physiologic sources and one noise source. Thus, consistent with implementations of the current subject matter physiologic sources may be distinguished from noise sources based on their statistics and the statistics of the respiratory and ballistocardiogram parameters. As shown in FIG. 12A, the demixing operation at 1214 may follow from the determination at 1208 that there is at least one physiological source on the article.

Figure 12B:
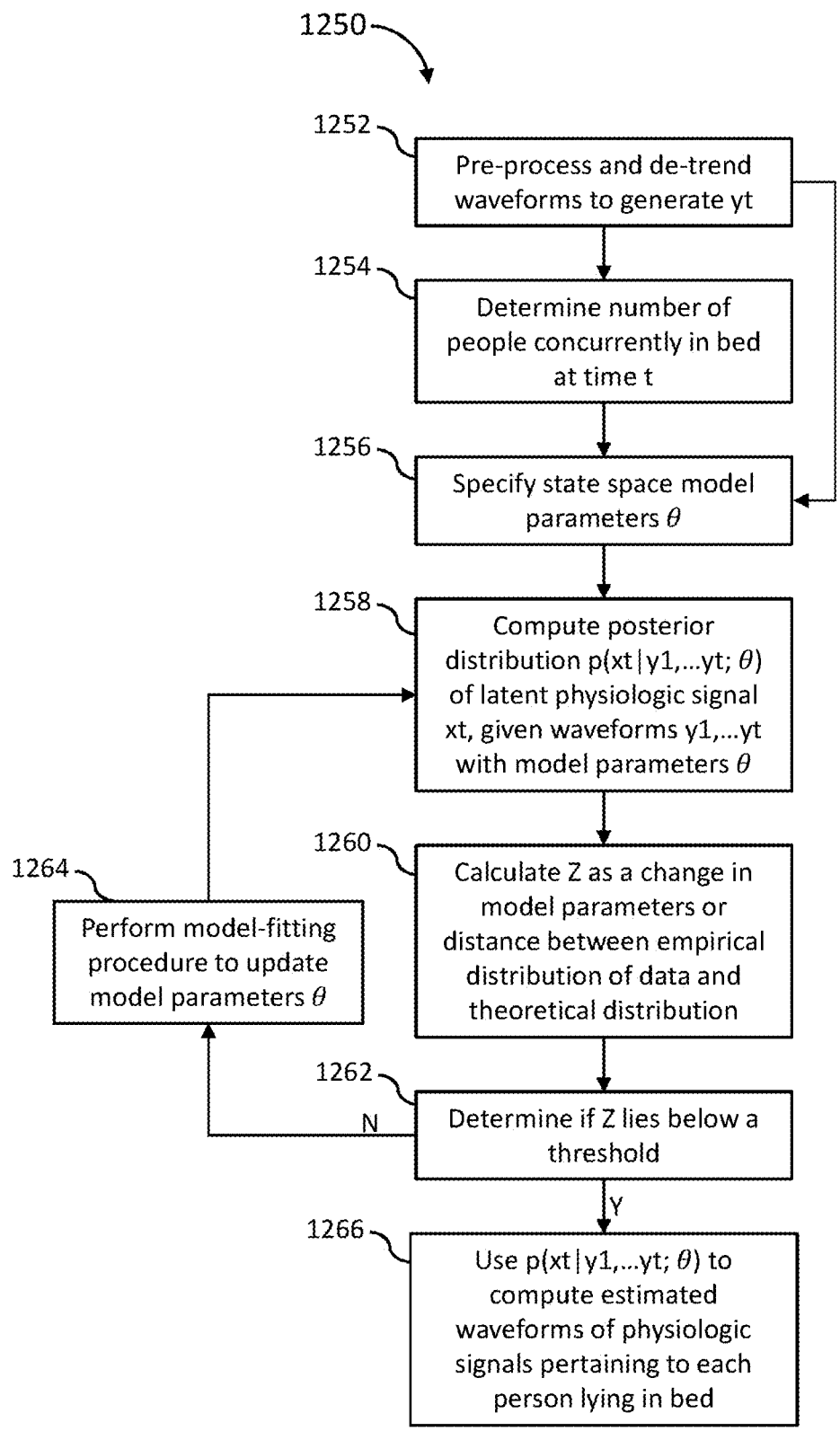
FIG. 12B depicts a flowchart illustrating a process consistent with implementations of the current subject matter.

With reference to flowchart 1250 of FIG. 12B, an example process consistent with implementations of the current subject matter is provided. In particular, the flowchart 1250 illustrates aspects of the demixing operation (1214 in FIG. 12A). Other signal demixing operations may be used with aspects of the current subject matter.

At 1252 of FIG. 12B, the force signals are processed (e.g., conditioned by pre-processing and de-trending the received force data to generate $y_t$. At 1254, the number of people (e.g., physiological sources) that are on the article (e.g., a bed) may be determined. As described with reference to FIG. 12A, this determination may be based on the force data and the resulting physiological signals. As also described with reference to FIG. 12A, consistent with implementations of the current subject matter, it is not necessary to determine in advance the number of physiological sources on the article, as the results of the demixing operation will indicate the number of physiological sources.

At 1256, following 1252 or 1254, state space model parameters θ are specified. As an example, suppose that it has been determined that two people are concurrently in the bed at time t for t a discrete time variable (e.g., after sampling) between 1 and integer T. In such a case, the source physiologic signal (e.g., respiration or ballistocardiogram) from each person at time t may be modeled as a length-two vector $X_t$. Assuming there is stochastic continuity in across time, a state space model of the form (1) may be specified:

$$X_t = A\,X_{t-1} + W_t \quad (1),$$

where $X_t$ is a length-two vector, A is a 2×2 matrix, and $W_t$ is a length-two vector pertaining to Gaussian random variables independent across time with mean zero and covariance matrix $K_W$.

In this example, assuming measurements at four legs of a bed, $Y_t$ may be modeled at time t as a length 4 vector according to the following statistical model p(y|x):

$$Y_t = L_0 X_t + L_1 X_{t-1} + \ldots + L_k X_{t-k} + N_t \quad (2),$$

where k is the order of the dependence, $L_0, \ldots, L_k$ are 4×2 matrices, and $N_t$ is a length 4 Gaussian random vector, independent across time, with mean zero and covariance matrix $K_N$. For this example, the model parameters are given by $\theta = (K_W, K_N, L_1, \ldots, L_K)$.

At 1258, posterior distribution $p(x_1, \ldots x_t | y_1, \ldots y_t; \theta)$ of latent physiologic signal $x_t$ is computed, given waveforms $y_1, \ldots y_t$ with model parameters θ. Bayesian inference techniques may be used to compute the posterior distribution $p(x_1, \ldots x_t | y_1, \ldots y_t; \theta)$ at time t. For instance, in accordance with the above example, for any theta, the posterior distribution is Gaussian and the mean and covariance can be updated recursively with the Kalman smoother. More generally, if $-\log p(x_1, \ldots x_t, y_1, \ldots y_t; \theta)$ is convex in $x_1, \ldots x_t$ (which occurs in the Gaussian example as a special case), generating samples $x'_1, \ldots x'^t$ from the posterior distribution can be performed efficiently with parallelized convex optimization techniques. More general versions of approaches to generate samples from the posterior include the use of Generative Adversarial Networks using deep neural networks.

At 1260, Z is calculated as a change in model parameters or distance between empirical distribution of data and theoretical distribution. The change between the current and previous model parameters may be computed to quantify convergence. As an example, for the above linear Gaussian example, the difference between the previous version of theta and its current version may be computed, and Z may be selected as the largest change in absolute value across each component. As another example, given samples $x'_1, \ldots x'_t$ from the posterior distribution, a nonparametric two-sample test statistic Z may be implemented by first computing the empirical distribution $P_y$ of $y_1, \ldots y_t$. Next, the empirical distribution $P_y{'}$ of newly generated $y'_1, \ldots y'_t$ may be computed from (2) using the posterior samples $x'_1, \ldots x'_t$ in the equation. The Wasserstein distance or an entropy-smoothed version may be calculated between these two empirical distributions.

At 1262, a determination is made if Z lies below a threshold. A threshold pertaining to convergence or a nonparametric distribution-free threshold may be specified to obtain a threshold for convergence that contains a statistical significance guarantee (e.g. 95% confidence).

At 1264, if Z does not lie below the threshold, a model-fitting procedure may be done to update model parameters θ. Updating the estimate of θ may be done iteratively, for example with the EM algorithm, by using samples $x'_1, \ldots x'_t$ from the posterior $p(x_1, \ldots x_t | y_t; \ldots y_t; \theta)$ and maximizing an expected value of the log of $p(x_1, \ldots x_t, y_1, \ldots y_t; \theta)$ using an average based upon samples $x'_1, \ldots x'_t$.

At 1266, if Z lies below the threshold, $p(x_t | y_1, \ldots y_t; \theta)$ may be used to compute estimated waveforms of source physiologic signals pertaining to each person lying in bed. With the posterior distribution, an estimate of the waveforms may be computed by solving a least squares or maximum a posteriori (MAP) estimation procedure. For the aforementioned Gaussian example, least squares and MAP estimation have the same solution which can be solved efficiently with the Kalman smoother. For a case for which $-\log p(x_1, \ldots x_t, y_1, \ldots y_t; \theta)$ is convex in $x_1, \ldots x_t$, the MAP estimate may be solved iteratively and in a modularized manner where one sub-procedure is the Kalman smoother. For the same context where which $-\log p(x_1, \ldots x_t, y_1, \ldots y_t; \theta)$ is convex in $x_1, \ldots x_t$, the least squares estimate, which is the conditional expectation $E[X_t | Y_1 = y_1 \ldots Y_t = y^t]$, can be computed efficiently with parallelized convex optimization methods.

The health monitor system 100 according to aspects of the current subject matter is a non-contact adherence-independent home health monitoring system that longitudinally quantifies dynamic forces across diverse amplitudes and time scales to measure weight, respirations, and ballistocardiograms each night, as people sleep in the comfort of their home beds. Weights and respiratory signals are demixed even when users share the bed with a partner or pet. Finally, the incorporated technology is scalably manufacturable and thus inexpensive compared to implantable medical devices intended for the same purpose.

Consistent with implementations of the current subject matter, the health monitor system 100 may, by obtaining real-time force data and analyzing and detecting physiological parameters for one or more physiological sources, provide clinical data for diagnoses and/or treatment. For example, the extracted physiological parameters may be used to change dose of medication, prompt a clinical visit, initiate in real-time a treatment such as a nebulizer or other aerosolized treatment, alter a sleep apnea therapy treatment, and/or adjust position, temperature, or other attribute of the bed or room with the intent of modifying physiology.

Additionally, consistent with implementations of the current subject matter, notifications and/or information may be provided from the health monitor system 100 to one or more individuals, centers, or other system (e.g., a healthcare system). For example, notifications may be sent to the individuals, family, friends, healthcare providers, or the like. Reports or the like may be created and sent similar to the notifications.

Consistent with implementations of the current subject matter, the remote processing device 130 may identify a point of time at which a first user enters sleep. The identification may be based on the force data obtained from the sensors 120. For example, individuals tend to change position nearly continuously while awake but only episodically during sleep. The point of time at which the first user enters sleep may be based on a frequency of load distributions of the first user force data. A frequency of load distributions may be defined (based on for example a history or collection of gathered user data) as a threshold point for defining a state of sleep, where a point at or below the frequency is indicative of user sleep.

Consistent with implementations of the current subject matter, the remote processing device 130 may identify, from the source physiological signals, presence of obstructive sleep apneas. The presence of obstructive sleep apneas may be based on, for example, an amplitude of a respiratory signal. Consistent with implementations of the current subject matter, the remote processing device 130 may identify, from the source physiological signals, presence of central sleep apneas. The presence of central sleep apneas may be based on, for example, a lapse in the respiratory signal. Thus, consistent with implementations of the current subject matter, the health monitor system 100 may be utilized to aid in sleep studies and diagnoses and treatment of sleep disorders.

Figure 13:
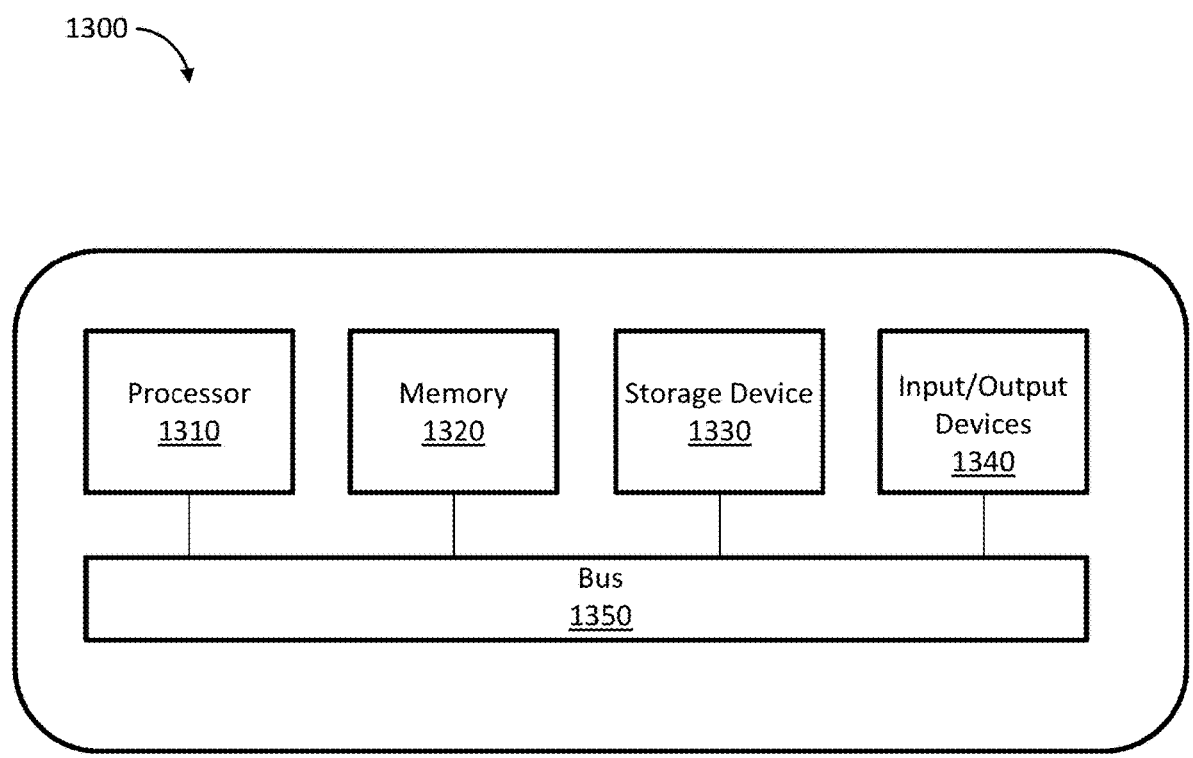
FIG. 13 depicts a block diagram illustrating a computing system consistent with implementations of the current subject matter.

FIG. 13 depicts a block diagram illustrating a computing system 1300 consistent with implementations of the current subject matter. Referring to FIG. 13, the computing system 1300 can be used to implement the health monitor system 100 and/or any components therein.

As shown in FIG. 13, the computing system 1300 can include a processor 1310, a memory 1320, a storage device 1330, and input/output devices 1340. The processor 1310, the memory 1320, the storage device 1330, and the input/output devices 1340 can be interconnected via a system bus 1350. The processor 1310 is capable of processing instructions for execution within the computing system 1300. Such executed instructions can implement one or more components of, for example, the health monitor system 100. In some implementations of the current subject matter, the processor 1310 can be a single-threaded processor. Alternately, the processor 1310 can be a multi-threaded processor. The processor 1310 is capable of processing instructions stored in the memory 1320 and/or on the storage device 1330 to display graphical information for a user interface provided via the input/output device 1340.

The memory 1320 is a computer readable medium such as volatile or non-volatile that stores information within the computing system 1300. The memory 1320 can store data structures representing configuration object databases, for example. The storage device 1330 is capable of providing persistent storage for the computing system 1300. The storage device 1330 can be a floppy disk device, a hard disk device, an optical disk device, or a tape device, or other suitable persistent storage means. The input/output device 1340 provides input/output operations for the computing system 1300. In some implementations of the current subject matter, the input/output device 1340 includes a keyboard and/or pointing device. In various implementations, the input/output device 1340 includes a display unit for displaying graphical user interfaces.

According to some implementations of the current subject matter, the input/output device 1340 can provide input/output operations for a network device. For example, the input/output device 1340 can include Ethernet ports or other networking ports to communicate with one or more wired and/or wireless networks (e.g., a local area network (LAN), a wide area network (WAN), the Internet).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. For example, the logic flows may include different and/or additional operations than shown without departing from the scope of the present disclosure. One or more operations of the logic flows may be repeated and/or omitted without departing from the scope of the present disclosure. Other implementations may be within the scope of the following claims.

What is claimed is:

1. A system, comprising:
a plurality of sensors, each of the plurality of sensors configured to engage with an article on which a first user is positioned, and each of the plurality of sensors configured to measure force;
a communication module in wired communication with each of the plurality of sensors, wherein the communication module receives force data transmitted from each of the plurality of sensors; and
an apparatus comprising:
at least one data processor; and
at least one memory storing instructions which, when executed by the at least one data processor, cause the apparatus to at least:
receive, from the communication module, the force data transmitted from each of the plurality of sensors;
transform, in response to a change in the force data indicative of a change in a load on the article, the force data from each of the plurality of sensors into a corresponding plurality of physiological signals; and
determine, based on the plurality of physiological signals, a source physiological signal for each of a plurality of physiological sources;
wherein the determination of the source physiological signal for each of the plurality of physiological sources further comprises:
separating into components each of the plurality of physiological signals, wherein the components correspond to each of the plurality of physiological sources at each of the plurality of sensors, and wherein the separating further comprises:
pre-processing each of the plurality of physiological signals,
specifying a state space of model parameters, each of the model parameters of the state space describing an aspect of the plurality of physiological signals,
determining a posterior distribution of the plurality of physiological signals,
determining a change in at least a first parameter of the model parameters of the state space,
determining if the change in at least the first parameter of the model parameters of the state space is below a predefined threshold, and
in response to the change in the at least the first model parameter being less than the predefine threshold, using the posterior distribution to estimate, for each of the plurality of physiological signals, waveforms of the separated components; and
compositing the separated components to form the source physiological signal for each of the plurality of physiological sources, and
wherein the transforming the force data further comprises time-domain or frequency-domain filtering the force data to obtain a plurality of respiratory signals corresponding to each of the plurality of sensors.

2. The system of claim 1, wherein the apparatus is further configured to determine a number of physiological sources on the article, and, based on the determination of the plurality of physiological sources on the article, the physiological signals are based on the force data from at least two of the plurality of sensors.

3. The system of claim 1, wherein a source respiratory signal is determined, based on the plurality of respiratory signals, for each of the plurality of physiological sources, and wherein the execution of the instructions further cause the apparatus to at least:
identify, from the source respiratory signal for each of the plurality of physiological sources, one or more respiratory parameters.

4. The system of claim 1, wherein transforming the force data comprises time-domain and/or frequency-domain filtering the force data to obtain a plurality of ballistocardiogram signals corresponding to each of the plurality of sensors.

5. The system of claim 4, wherein a source ballistocardiogram signal is determined, based on the plurality of ballistocardiogram signals, for each of the plurality of physiological sources, and wherein the execution of the instructions further cause the apparatus to at least:
identify, from the source ballistocardiogram signal for each of the plurality of physiological sources, one or more ballistocardiogram parameters.

6. The system of claim 1, wherein the change in the force data indicative of the change in the load on the article is determined based on identifying the change in the force data greater than the predefined threshold of force for a predefined duration threshold.

7. The system of claim 2, wherein the determination of the number of plurality of physiological sources on the article is based on identification of alterations in the physiological signals transformed from the force data.

8. A method, comprising:
receiving, by a remote processing device and from a communication module in wired communication with a plurality of sensors, force data transmitted from the plurality of sensors, wherein each of the plurality of sensors is configured to engage with a member of an article on which a first user is positioned, and further wherein each of the plurality of sensors is configured to measure force;
transforming, by the remote processing device and in response to a change in the force data indicative of a change in a load on the article, the force data from each of the plurality of sensors into a plurality of physiological signals; and
determining, by the remote processing device and based on the plurality of physiological signals, a source physiological signal for each of a plurality of physiological sources;
wherein the determination of the source physiological signal for each of the plurality of physiological sources comprises:
separating into components each of the plurality of physiological signals, wherein the components correspond to each of the plurality of physiological sources at each of the plurality of sensors, and wherein the separating further comprises:
pre-processing each of the plurality of physiological signals,
specifying a state space of model parameters, each of the model parameters of the state space describing an aspect of the plurality of physiological signals,
determining a posterior distribution of the physiological signals,
determining a change in at least a first parameter of the model parameters of the state space,
determining if the change in at least the first parameter of the model parameters of the state space is below a predefined threshold, and
in response to the change in at least the first model parameter being less than the predefined threshold, using the posterior distribution to estimate, for each of the plurality of physiological signals, waveforms of the separated components; and
compositing the separated components to form the source physiological signal for each of the plurality of physiological sources, and
wherein the transforming the force data comprises time-domain or frequency-domain filtering the force data to obtain a plurality of respiratory signals corresponding to each of the plurality of sensors.

9. The method of claim 8, wherein the determination of the source physiological signal for each of the plurality of physiological sources is based on a model for each of the plurality of physiological sources, wherein each model comprises the components, the components defining a contribution of a respective physiological source to each of the plurality of physiological sources.

10. The method of claim 8 further comprising determining a number of physiological sources on the article, wherein, based on the determination of the plurality of physiological sources on the article, the physiological signals are based on the force data from at least two of the plurality of sensors.

11. The method of claim 8, wherein a source respiratory signal is determined, based on the plurality of respiratory signals, for each of the plurality of physiological sources, and wherein the method further comprises:
identifying, from the source respiratory signal for each of the plurality of physiological sources, one or more respiratory parameters.

12. The method of claim 8, wherein transforming the force data comprises time-domain and/or frequency-domain filtering the force data to obtain a plurality of ballistocardiogram signals corresponding to each of the plurality of sensors.

13. The method of claim 12, wherein a source ballistocardiogram signal is determined, based on the plurality of ballistocardiogram signals, for each of the plurality of physiological sources, and wherein the method further comprises:
identifying, from the source ballistocardiogram signal for each of the plurality of physiological sources, one or more ballistocardiogram parameters.

14. The method of claim 8, wherein the change in the force data indicative of the change in the load on the article is determined based on identifying the change in the force data greater than the predefined threshold of force for a predefined duration threshold.

15. The method of claim 10, wherein the determination of the number of plurality of physiological sources on the article is based on identification of alterations in the physiological signals transformed from the force data.

16. An apparatus, comprising:
at least one data processor; and
at least one memory storing instructions which, when executed by the at least one data processor, cause the apparatus to at least:
receive, from a communication module in wired communication with a plurality of sensors, force data transmitted from the plurality of sensors, wherein each of the plurality of sensors is configured to engage with a member of an article on which a first user is positioned, and further wherein each of the plurality of sensors is configured to measure force;

transform, in response to a change in the force data indicative of a change in a load on the article, the force data from each of the plurality of sensors into a plurality of physiological signals; and determine, based on the plurality of physiological signals, a source physiological signal for each of a plurality of physiological sources;

wherein the determination of the source physiological signal for each of the plurality of physiological sources comprises:

separating into components each of the plurality of physiological signals, wherein the components correspond to each of the plurality of physiological sources at each of the plurality of sensors, and wherein the separating further comprises:

pre-processing each of the plurality of physiological signals, specifying a state space of model parameters, each of the model parameters of the state space describing an aspect of the plurality of physiological signals, determining a posterior distribution of the physiological signals, determining a change in at least a first parameter of the model parameters of the state space, determining if the change in at least the first parameter of the model parameters of the state space is below a predefined threshold, and in response to the change in the at least the first model parameter being less than the predefined threshold, using the posterior distribution to estimate, for each of the plurality of physiological signals, waveforms of the separated components; and compositing the separated components to form the source physiological signal for each of the plurality of physiological sources, and wherein the transforming the force data comprises time-domain or frequency- domain filtering the force data to obtain a plurality of respiratory signals corresponding to each of the plurality of sensors.

17. A non-transitory computer-readable storage medium including program code, which when executed by at least one data processor, causes operations comprising:

receiving, by a remote processing device and from a communication module in wired communication with a plurality of sensors, force data transmitted from the plurality of sensors, wherein each of the plurality of sensors is configured to engage with a member of an article on which a first user is positioned, and further wherein each of the plurality of sensors is configured to measure force;

transforming, by the remote processing device and in response to a change in the force data indicative of a change in a load on the article, the force data from each of the plurality of sensors into a plurality of physiological signals; and determining, by the remote processing device and based on the plurality of physiological signals, a source physiological signal for each of a plurality of physiological sources;

wherein the determination of the source physiological signal for each of the plurality of physiological sources comprises:

separating into components each of the plurality of physiological signals, wherein the components correspond to each of the plurality of physiological sources at each of the plurality of sensors, and wherein the separating further comprises:

pre-processing each of the plurality of physiological signals, specifying a state space of model parameters, each of the model parameters of the state space describing an aspect of the plurality of physiological signals, determining a posterior distribution of the physiological signals, determining a change in at least a first parameter of the model parameters of the state space, determining if the change in at least the first parameter of the model parameters of the state space is below a predefined threshold, and in response to the change in the at least the first model parameter being less than the predefined threshold, using the posterior distribution to estimate, for each of the plurality of physiological signals, waveforms of the separated components; and compositing the separated components to form the source physiological signal for each of the plurality of physiological sources, and wherein the transforming the force data comprises time-domain or frequency-domain filtering the force data to obtain a plurality of respiratory signals corresponding to each of the plurality of sensors.

* * * * *